(12) United States Patent
Gunderson

(10) Patent No.: US 12,690,821 B2
(45) Date of Patent: Jul. 28, 2026

(54) PREDICTING A LIKELIHOOD OF A FALL BASED ON WALKING BUT NOT TALKING

(71) Applicant: Medtronic, Inc., Minneapolis, MN (US)

(72) Inventor: Bruce D. Gunderson, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 249 days.

(21) Appl. No.: 18/567,292

(22) PCT Filed: Jun. 9, 2022

(86) PCT No.: PCT/US2022/032751
§ 371 (c)(1),
(2) Date: Dec. 5, 2023

(87) PCT Pub. No.: WO2023/283015
PCT Pub. Date: Jan. 12, 2023

(65) Prior Publication Data
US 2024/0260908 A1 Aug. 8, 2024

Related U.S. Application Data

(60) Provisional application No. 63/219,595, filed on Jul. 8, 2021.

(51) Int. Cl.
*A61B 5/00* (2006.01)
*A61B 5/11* (2006.01)

(52) U.S. Cl.
CPC .......... *A61B 5/7275* (2013.01); *A61B 5/1123* (2013.01); *A61B 5/1126* (2013.01);
(Continued)

(58) Field of Classification Search
CPC ... A61B 5/1116; A61B 5/1117; A61B 5/1123; A61B 5/1126; A61B 5/4848;
(Continued)

(56) References Cited

U.S. PATENT DOCUMENTS 9,801,568 B2 10/2017 Ziaie et al.
10,299,736 B2 5/2019 Najafi et al.
(Continued)

FOREIGN PATENT DOCUMENTS

WO 2009156936 A2 12/2009
WO 2018127506 A1 7/2018
WO 2019213399 A1 11/2019

OTHER PUBLICATIONS

Ayers et al., "Walking While Talking and Falls in Aging," Gerontology, vol. 60, No. 2, Nov. 2013, pp. 108-113.
(Continued)

*Primary Examiner* — Devin B Henson
(74) *Attorney, Agent, or Firm* — Shumaker & Sieffert, P.A.

(57) ABSTRACT

An example device or system and method includes accelerometer circuitry configured to generate at least one signal, a microphone configured to capture a voice of a person, a memory, and processing circuitry communicatively coupled to the accelerometer circuitry, the microphone, and the memory. The processing circuitry is configured to determine when the person is walking based on the at least one signal and determine when the person is talking based on the captured voice. The processing circuitry is configured to determine a risk of falling based on the determination of when the person is walking and the determination of when the person is talking.

16 Claims, 12 Drawing Sheets

(52) U.S. Cl.
CPC ............ *A61B 5/4848* (2013.01); *A61B 5/746*
(2013.01); *A61B 5/7475* (2013.01); *A61B*
*2562/0204* (2013.01); *A61B 2562/0219*
(2013.01)

(58) Field of Classification Search
CPC ..... A61B 5/7275; A61B 5/746; A61B 5/7475;
A61B 5/749; A61B 2562/0204; A61B
2562/0219
See application file for complete search history.

(56) References Cited

U.S. PATENT DOCUMENTS

| | | | |
|---|---|---|---|
| 10,709,376 B2 | | 7/2020 | De Vries et al. |
| 11,189,149 B2 * | | 11/2021 | Stenlund ............... H04W 12/06 |
| 2001/0034583 A1 * | 10/2001 | Flentov ..................... G01P 3/50 |
| | | | 702/142 |
| 2018/0035920 A1 | 2/2018 | Gunderson et al. |
| 2018/0233018 A1 | 8/2018 | Burwinkel et al. |
| 2020/0118689 A1 | 4/2020 | Luthy et al. |
| 2020/0170548 A1 | 6/2020 | Hausdorff et al. |
| 2021/0045656 A1 * | 2/2021 | Rahman ................. A61B 7/003 |
| 2024/0285190 A1 * | 8/2024 | Bhowmik .............. A61B 5/112 |

OTHER PUBLICATIONS

Beauchet et al., "Stops Walking When Talking: a Predictor of Falls
in Older Adults?," European Journal of Neurology, vol. 16, No. 7,
Jul. 2009, pp. 786-795.
Lundin-Olsson et al., "Stops Walking When Talking as a Predictor
of Falls in Elderly People," The Lancet, vol. 349, No. 9052, Mar. 1,
1997, p. 617.

* cited by examiner

EXTERNAL
DEVICE
30C

DETERMINE WHEN A PERSON IS WALKING BASED ON AT LEAST ONE SIGNAL FROM ACCELEROMETER CIRCUITRY

DETERMINE WHEN THE PERSON IS TALKING BASED ON A CAPTURED VOICE FROM A MICROPHONE

DETERMINE A RISK OF FALLING BASED ON THE DETERMINATION OF WHEN THE PERSON IS WALKING AND THE DETERMINATION OF WHEN THE PERSON IS TALKING

PREDICTING A LIKELIHOOD OF A FALL BASED ON WALKING BUT NOT TALKING

This application is a national stage application under 35 U.S.C. § 371 of PCT Application No. PCT/US2022/032751, filed Jun. 9, 2022, which claims priority to and the benefit of U.S. Provisional Patent Application No. 63/219,595, filed Jul. 8, 2021, the entire contents of each of which are incorporated by reference.

TECHNICAL FIELD

The disclosure relates generally to devices, systems, and techniques, and more particularly to devices, systems, and techniques to predict the likelihood that a person, such as a patient, may fall.

BACKGROUND

Implantable medical devices (IMDs) and external, e.g., wearable, medical devices, including implantable pacemakers and implantable cardioverter-defibrillators (ICDs) and insertable cardiac monitors without therapies (e.g., Medtronic LINQ™ or LINQ II™), record cardiac electrogram (EGM) signals for sensing cardiac events, e.g., P-waves and R-waves. IMDs detect episodes of bradycardia, tachycardia and/or fibrillation from the sensed cardiac events, and some IMDs respond to the episodes as needed with pacing therapy or high-voltage anti-tachyarrhythmia shocks, e.g., cardioversion or defibrillation shocks. These and other medical devices may include, or be part of a system that includes, sensors that generate other physiological-based signals, such as signals that vary based on patient movement or activity, cardiovascular pressure, blood oxygen saturation, edema, or thoracic impedance.

SUMMARY

In general, this disclosure is directed to techniques for determining a risk that a person may fall based on whether the person talks while they are walking. More particularly, this disclosure contemplates a device or system that monitors a person for walking and talking. The device or system of this disclosure may include a smart phone, a wearable device, such as a smart watch or fitness monitor, an implanted medical device, or the like.

In one example, a system includes accelerometer circuitry configured to generate at least one signal indicative of a person walking; a microphone configured to capture a voice of the person; a memory; and processing circuitry communicatively coupled to the accelerometer circuitry, the microphone, and the memory configured to: determine when the person is walking based on the at least one signal; determine when the person is talking based on the captured voice; and determine a risk of falling based on the determination of when the person is walking and the determination of when the person is talking.

In other examples, a method includes determining, by processing circuitry, when a person is walking based on at least one signal from accelerometer circuitry; determining, by processing circuitry, when the person is talking based on a captured voice from a microphone; and determining a risk of falling based on the determination of when the person is walking and the determination of when the person is talking.

In other examples, a non-transitory computer-readable storage medium includes instructions, that when executed by processing circuitry, cause the processing circuitry to:

determine when a person is walking based on at least one signal for accelerometer circuitry; determine when the person is talking based on a captured voice from a microphone; and determine a risk of falling based on the determination of when the person is walking and the determination of when the person is talking.

This summary is intended to provide an overview of the subject matter described in this disclosure. It is not intended to provide an exclusive or exhaustive explanation of the apparatus and methods described in detail within the accompanying drawings and description below. The details of one or more aspects of the disclosure are set forth in the accompanying drawings and the description below.

DETAILED DESCRIPTION

Figure 1:
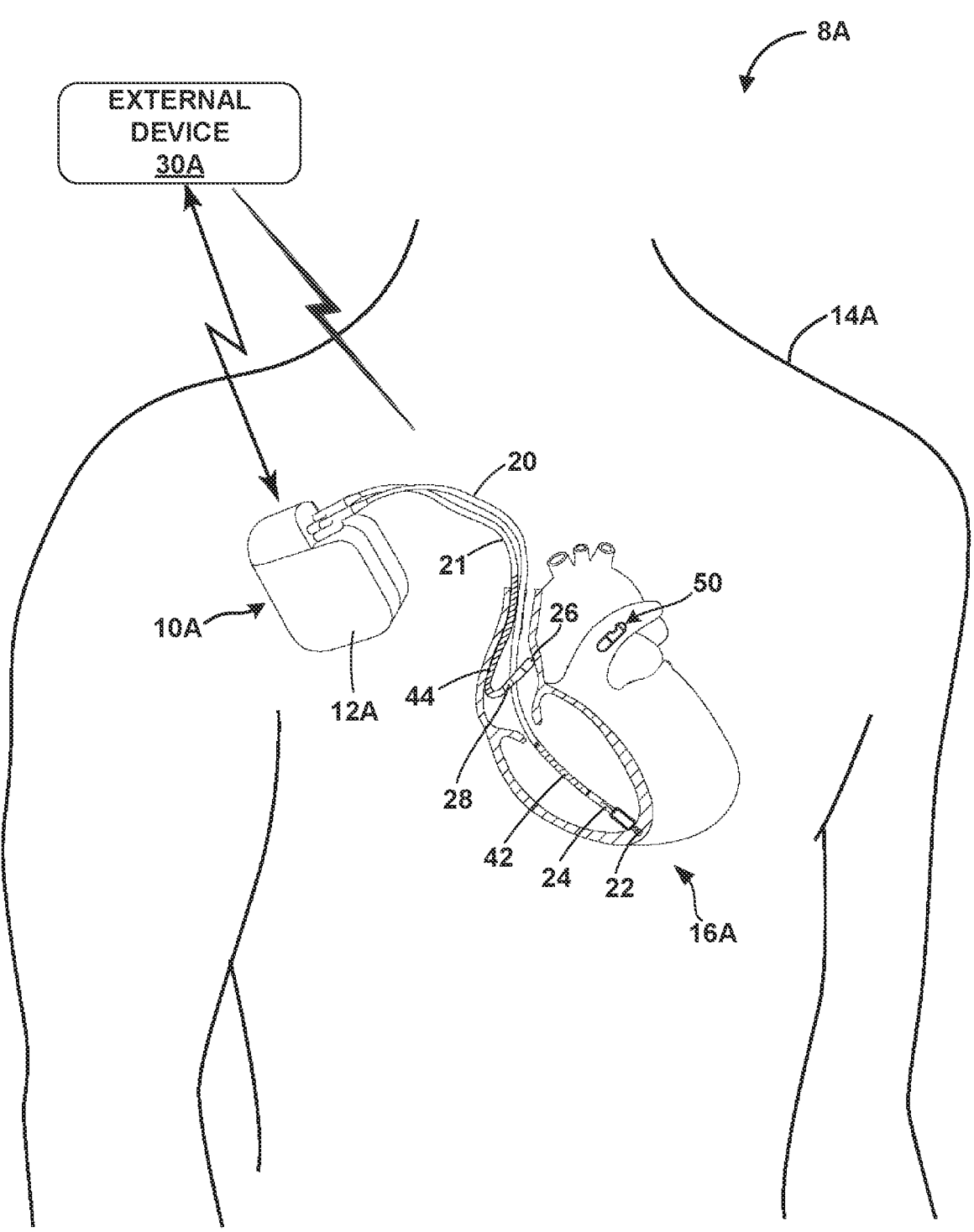
FIG. 1 is a conceptual drawing illustrating an example medical device system in conjunction with a patient.

Falls may cause a significant mortality and morbidity in the elderly. Predicting falls would provide an opportunity for an intervention that could potentially prevent the fall. A 1997 Lancet article titled "'Stops Walking When Talking' as a predictor of falls in elderly people" reports that people who are less steady and susceptible to falls are less able to walk and talk at the same time than people who are more steady and less susceptible to falls.

In some examples, a device or system may simultaneously monitor for the voice and activity level of a person. If the device or system determines a person is walking and talking at the same time, the fall risk may be relatively low. If the device or system determines that the person was both walking and talking at separate times, but not at the same time, then the fall risk may be relatively high.

Implantable medical devices (IMDs) including implantable pacemakers and implantable cardioverter-defibrillators (ICDs), and external, e.g., wearable devices, may record cardiac electrogram (EGM) signals for sensing cardiac events, e.g., P-waves and R-waves. IMDs detect episodes of bradycardia, tachycardia and/or fibrillation from the sensed cardiac events, and some IMDs respond to the episodes as needed with pacing therapy or high-voltage anti-tachyarrhythmia shocks, e.g., cardioversion or defibrillation shocks. These and other devices may include, or be part of a system that includes, sensors that generate other physiologicalbased signals, such as signals that vary based on patient movement or activity, such as walking, cardiovascular pressure, blood oxygen saturation, edema, or thoracic impedance. Smart phones, wearable devices, such as smart watches or fitness monitors, and the like may also include sensors that generate signals indicative of a person walking.

Additionally, some devices such as IMDs, smart phones, and other devices may include microphones which may capture sounds, such as a voice of a person or sounds of a person speaking. Processing circuitry may use a captured voice to determine whether a specific person is speaking. For example, there are many available algorithms that may use voice biometrics to identify a voice of a specific person. By using voice biometrics to identify a particular person speaking, processing circuitry may exclude non-matching voices when determining if the particular person is talking while walking. For example, processing circuitry may create a voice template through the use of a microphone in the device or system, such as an IMD microphone, smart phone microphone, wearable device microphone, or the like. The voice template may be stored in memory of the device or memory external to the device. In some examples, the device microphone may continuously check for a voice match with the stored template and store beginning and ending times of voice matches.

According to the features or aspects of this disclosure, processing circuitry may determine when a person is walking based on at least one signal indicative of a person walking and determine when a person is talking based on a captured voice. Processing circuitry may determine a risk of falling based on the determination of when the person is walking and the determination of when the person is talking.

For example, a device or system, according to certain features or aspects of this disclosure, includes accelerometer circuitry configured to generate at least one signal indicative of a person walking, a microphone configured to capture a voice of a person, as well as processing circuitry configured to match the voice of the person to a voice template and calculate a risk of the person falling based on whether the person is talking while they are walking. Such an implementation may, among other things, provide an objective measure of change (or not) in well-being to help guide therapies. For example, determining whether a person is talking while walking can help determine whether health is improving, declining, or stable. Although not so limited, an appreciation of the various aspects of the present disclosure may be gained from the following discussion in connection with the figures. While this disclosure may provide examples, including identifying devices or systems that may be configured to implement the techniques described herein, these identifications are not meant to be limiting. While primarily discussed herein in the context of an IMD and a patient, any device having an accelerometer and/or a microphone may be used to implement the techniques of this disclosure for any person. For example, a smart phone, or wearable device, such as a smart watch or fitness monitoring device, may be used to implement the techniques of this disclosure.

FIG. 1 is a conceptual drawing illustrating an example medical device system 8A in conjunction with a patient 14A. Medical device system 8A is an example of a medical device system configured to implement the techniques described herein for determining a risk of falling based on whether the person is talking while walking. Although not depicted in FIG. 1, one or more devices of medical device system 8A may include accelerometer circuitry configured to generate at least one signal indicative of a person (e.g., patient 14A) walking and a microphone configured to capture a voice of the person. In the illustrated example, medical device system 8A includes an implantable medical device (IMD) 10A coupled to a ventricular lead 20 and an atrial lead 21. IMD 10A is an implantable cardioverter-defibrillator (ICD) capable of delivering pacing, cardioversion and defibrillation therapy to the heart 16A of a patient 14A, and will be referred to as ICD 10A hereafter.

Ventricular lead 20 and atrial lead 21 are electrically coupled to ICD 10A and extend into the heart 16A of patient 14A. Ventricular lead 20 includes electrodes 22 and 24 shown positioned on the lead in the right ventricle (RV) of patient 14A for sensing ventricular EGM signals and pacing in the RV. Atrial lead 21 includes electrodes 26 and 28 positioned on the lead in the patient's right atrium (RA) for sensing atrial EGM signals and pacing in the RA.

Ventricular lead 20 additionally carries a high voltage coil electrode 42, and atrial lead 21 carries a high voltage coil electrode 44, used to deliver cardioversion and defibrillation shocks. The term "anti-tachyarrhythmia shock" may be used herein to refer to both cardioversion shocks and defibrillation shocks. In other examples, ventricular lead 20 may carry both of high voltage coil electrodes 42 and 44, or may carry a high voltage coil electrode in addition to those illustrated in the example of FIG. 1.

ICD 10A may use both ventricular lead 20 and atrial lead 21 to acquire cardiac electrogram (EGM) signals from patient 14A and to deliver therapy in response to the acquired data. Medical device system 8A is shown as having a dual chamber ICD configuration, but other examples may include one or more additional leads, such as a coronary sinus lead extending into the right atrium, through the coronary sinus and into a cardiac vein to position electrodes along the left ventricle (LV) for sensing LV EGM signals and delivering pacing pulses to the LV. In other examples, a medical device system may be a single chamber system, or otherwise not include atrial lead 21.

Processing circuitry, sensing circuitry, and other circuitry configured for performing the techniques described herein are housed within a sealed housing 12. Housing 12 (or a portion thereof) may be conductive so as to serve as an electrode for pacing or sensing or as an active electrode during defibrillation. As such, housing 12 is also referred to herein as "housing electrode" 12.

ICD 10A may transmit EGM signal data and cardiac rhythm episode data acquired by ICD 10A, as well as data regarding delivery of therapy by ICD 10A, as well as data in manipulated and/or in raw form, possibly compressed, encoded, and/or the like, associated with a patient walking, as determined from accelerometer circuitry-generated signal(s), and/or talking, as determined from a voice captured by a microphone, to an external device 30A. External device 30A may be a computing device, e.g., used in a home, ambulatory, clinic, or hospital setting, to communicate with ICD 10A via wireless telemetry. External device 30A may be coupled to a remote monitoring system, such as Carelink®, available from Medtronic plc, of Dublin, Ireland. External device 30A may be, for example, a programmer, external monitor, or consumer device, e.g., a wearable device or a smart phone, such as the iPhone® by Apple Inc. of Cupertino, CA. In some examples, ICD 10A may include the accelerometer circuitry, the microphone, or both the accelerometer circuitry and the microphone. In some examples, ICD 10A may not include the accelerometer circuitry or the microphone, and external device 30A may include the accelerometer circuitry and the microphone.

External device 30A may be used to program commands or operating parameters into ICD 10A for controlling its functioning, e.g., when configured as a programmer for ICD 10A. External device 30A may be used to interrogate ICD 10A to retrieve data, including device operational data as well as physiological data accumulated in memory of ICD 10A, such as data associated with a when patient 14A was walking, when patient 14A was talking, and/or a risk that patient 14A may fall based on when patient 14A was walking and when patient 14A was talking. The interrogation may be automatic, e.g., according to a schedule, or in response to a remote or local user command. Programmers, external monitors, and consumer devices are examples of external devices 30A that may be used to interrogate ICD 10A. Examples of communication techniques used by ICD 10A and external device 30A include radiofrequency (RF) telemetry, which may be an RF link established via Bluetooth®, wireless local area network, wireless wide area network, medical implant communication service (MICS) or other wireless connection.

In some examples, as illustrated in FIG. 1, medical device system 8A may also include a pressure-sensing IMD 50. In the illustrated example, pressure-sensing IMD 50 is implanted in the pulmonary artery of patient 14A. In some examples, one or more pressure-sensing IMDs 50 may additionally or alternatively be implanted within a chamber of heart 16A, or generally at other locations in the circulatory system.

In one example, pressure-sensing IMD 50 is configured to sense blood pressure of patient 14A. For example, pressure-sensing IMD 50 may be arranged in the pulmonary artery and be configured to sense the pressure of blood flowing from the right ventricle outflow tract (RVOT) from the right ventricle through the pulmonary valve to the pulmonary artery. Pressure-sensing IMD 50 may therefore directly measure pulmonary artery diastolic pressure (PAD) of patient 14A. The PAD value is a pressure value that can be employed in patient monitoring. For example, PAD may be used as a basis for evaluating congestive heart failure in patient 14A.

In other examples, however, pressure-sensing IMD 50 may be employed to measure blood pressure values other than PAD. For example, pressure-sensing IMD 50 may be arranged in the right ventricle of heart 16A to sense RV systolic or diastolic pressure, or may sense systolic or diastolic pressures at other locations of the cardiovascular system, such as within the pulmonary artery. As shown in FIG. 1, pressure-sensing IMD 50 is positioned in the main trunk of pulmonary artery 39. In other examples, a sensor, such as pressure-sensing IMD 50 may be either positioned in the right or left pulmonary artery beyond the bifurcation of the pulmonary artery.

Moreover, the placement of pressure-sensing IMD 50 is not restricted necessarily to the pulmonary side of the circulation. The pressure-sensing IMD 50 could potentially be placed in the systemic side of the circulation. For example, under certain conditions and with appropriate safety measures, pressure-sensing IMD 50 could even be placed in the left atrium, left ventricle, or aorta. Additionally, pressure-sensing IMD 50 is not restricted to placement within the cardiovascular system. For example, the pressure-sensing IMD 50 might be placed in the renal circulation. Placement of pressure-sensing IMD 50 in the renal circulation may be beneficial, for example, to monitor the degree of renal insufficiency in patient 14A based on the monitoring of pressure or some other indication of renal circulation by pressure-sensing IMD 50.

In some examples, pressure-sensing IMD 50 includes a pressure sensor configured to respond to the absolute pressure inside the pulmonary artery of patient 14A. Pressure-sensing IMD 50 may be, in such examples, any of a number of different types of pressure sensors. One form of pressure sensor that may be useful for measuring blood pressure is a capacitive pressure sensor. Another example pressure sensor is an inductive sensor. In some examples, pressure-sensing IMD 50 may also comprise a piezoelectric or piezoresistive pressure transducer. In some examples, pressure-sensing IMD 50 may comprise a flow sensor.

In one example, pressure-sensing IMD 50 comprises a leadless pressure sensor including capacitive pressure sensing elements configured to measure blood pressure within the pulmonary artery. Pressure-sensing IMD 50 may be in wireless communication with ICD 10A and/or external device 30A, e.g., in order to transmit blood pressure measurements to one or both of the devices. Pressure-sensing IMD 50 may employ, e.g., radio frequency (RF) or other telemetry techniques for communicating with ICD 10A and other devices, including, e.g., external device 30A. In another example, pressure-sensing IMD 50 may include a tissue conductance communication (TCC) system by which the device employs tissue of patient 14A as an electrical communication medium over which to send and receive information to and from ICD 10A and/or external device 30A.

Medical device system 8A is an example of a medical device system configured for determining a risk of falling based on the determination of when the person is walking and the determination of when the person is talking. Such techniques as contemplated may be performed by processing circuitry of medical device system 8A, such as processing circuitry of one or both of ICD 10A and external device 30A, individually, or collectively. Other example medical device systems that may be configured to implement the techniques are described with respect to FIGS. 2-9. Although described herein primarily in the context of implantable medical devices generating signals and, in some examples, delivering therapy, a system that implements the techniques described in this disclosure may additionally or alternatively include an external device, such as, a smart phone or wearable device, configured to perform one or more of generating at least one signal indicative of whether a person is walking (e.g., an accelerometer signal), capturing a voice of a person, determining when the person is walking based on the at least one signal, determining when the person is talking based on the captured voice, determining a risk of falling based on the determination of when the person is walking and the determination of when the person is talking, or perform other techniques of this disclosure.

Figure 2:
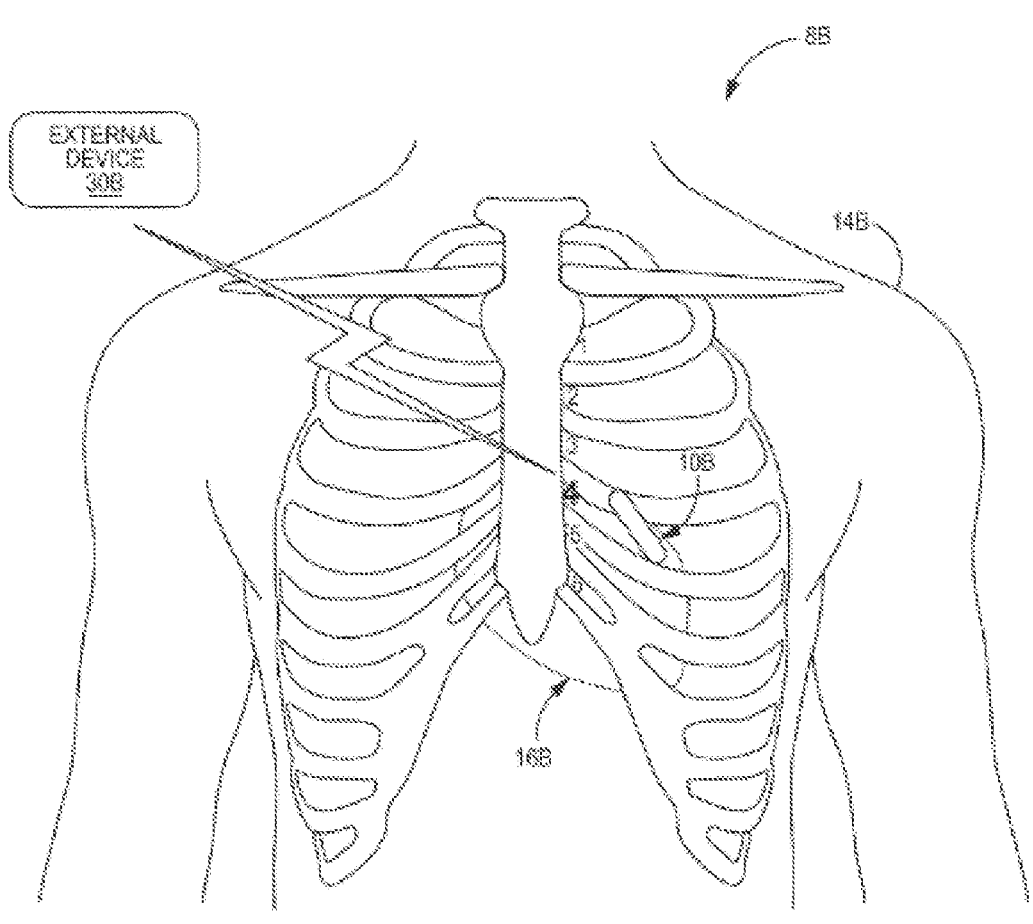
FIG. 2 is a conceptual drawing illustrating another example medical device system in conjunction with a patient.

FIG. 2 is a conceptual drawing illustrating another example medical device system 8B in conjunction with a patient 14B. Medical device system 8B is another example of a medical device system configured to implement the techniques described herein for determining a risk of falling based on a determination of when a person is walking and a determination of when a person is talking. In the illustrated example, medical device system 8B includes an IMD 10B and an external device 30B.

IMD 10B is an insertable cardiac monitor (ICM) capable of sensing and recording cardiac EGM signals from a position outside of heart 16B, and will be referred to as ICM 10B hereafter. Further, ICM 10B is capable of implementing one or more techniques for determining a risk of falling based on the determination of when the person is walking and the determination of when the person is talking in accordance with the present disclosure. In some examples, ICM 10B includes or is coupled to one or more additional sensors that generate one or more other physiological signals, such as signals that vary based on patient motion and/or posture (e.g., accelerometer circuitry), blood flow, or respiration. In some examples, ICM 10B may also include a microphone configured to capture a voice of patient 10B. ICM 10B may be implanted outside of the thorax of patient 14B, e.g., subcutaneously or submuscularly, such as the pectoral location illustrated in FIG. 2. In some examples, ICM 10B may take the form of a Reveal LINQ™ ICM, available from Medtronic plc, of Dublin, Ireland.

External device 30B may be configured in a manner substantially similar to that described above with respect to external device 30A and FIG. 1. External device 30B may wirelessly communicate with ICM 10B, e.g., to program the functionality of the ICM, and to retrieve recorded physiological signals and/or patient parameter values or scores, such as a risk of falling, or other data derived from such signals from the ICM. Both ICM 10B and external device 30B include processing circuitry, and the processing circuitry of either or both devices may perform the techniques described herein for determining a risk of falling, as discussed in further detail below.

Although not illustrated in the example of FIG. 2, a system configured to implement the techniques of this disclosure may include one or more implanted or external medical devices in addition to or instead of ICM 10B. For example, a medical device system may include a pressure sensing IMD 50, vascular ICD (e.g., ICD 10A of FIG. 1), extravascular ICD (e.g., ICD 10C of FIGS. 4A-5), or cardiac pacemaker (e.g., IPD 10D of FIGS. 4A-6 or a cardiac pacemaker implanted outside the heart but coupled to intracardiac or epicardial leads). One or more such devices may generate accelerometer signals and/or capture a voice of patient 14B, and include processing circuitry configured to perform, in whole or in part, the techniques described herein for determining a risk of falling. The implanted devices may communicate with each other and/or an external device 30, and one of the implanted or external devices may ultimately calculate a risk of falling based on the determination of when patient 14B is walking and when patient 14B is talking.

Figure 3:
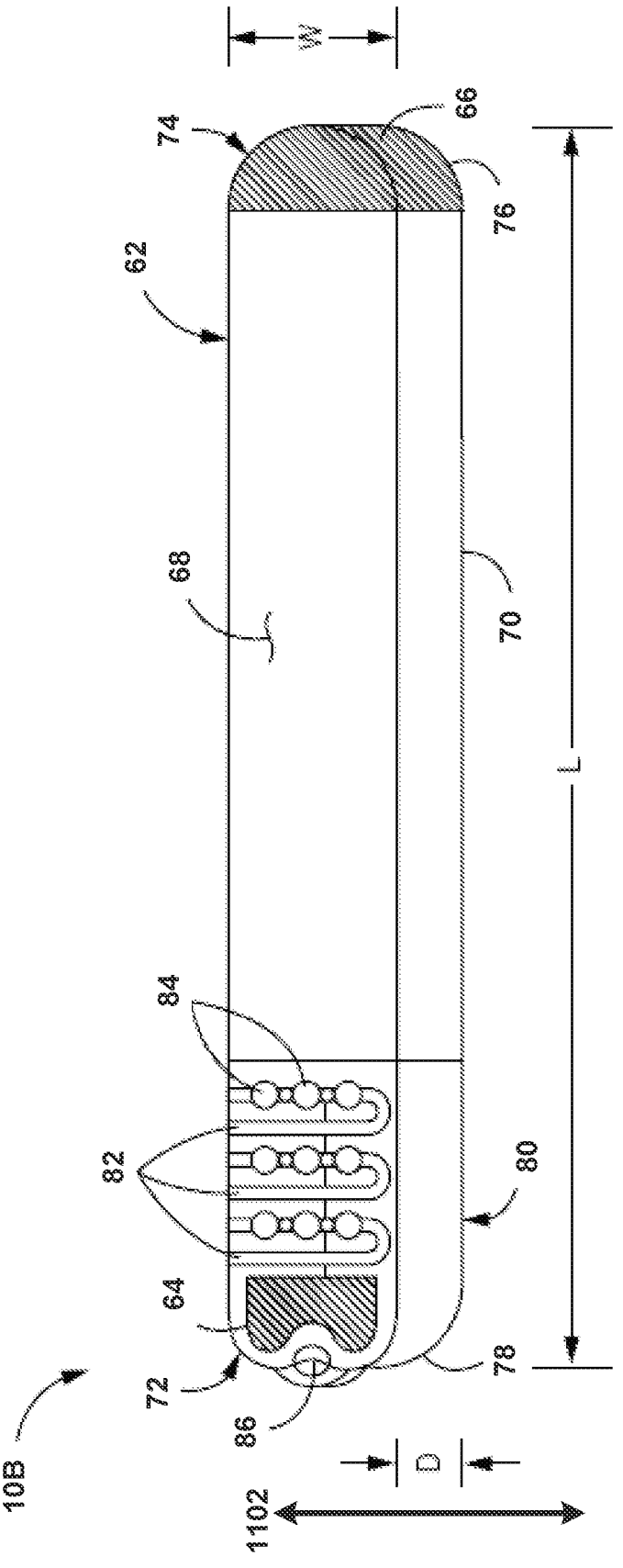
FIG. 3 is a perspective drawing illustrating an example configuration of the implantable cardiac monitor of FIG. 2.

FIG. 3 is a conceptual drawing illustrating an example configuration of ICM 10B. In the example shown in FIG. 3, ICM 300 may be embodied as a monitoring device having housing 62, proximal electrode 64 and distal electrode 66. Housing 62 may further comprise first major surface 68, second major surface 70, proximal end 72, and distal end 74. Housing 62 encloses electronic circuitry located inside the ICM 10B and protects the circuitry contained therein from body fluids. Electrical feedthroughs provide electrical connection of electrodes 64 and 66.

In the example shown in FIG. 3, ICM 10B is defined by a length L, a width W and thickness or depth D and is in the form of an elongated rectangular prism wherein the length L is much larger than the width W, which in turn is larger than the depth D. In one example, the geometry of the ICM 10B—in particular a width W greater than the depth D—is selected to allow ICM 10B to be inserted under the skin of patient 14B using a minimally invasive procedure and to remain in the desired orientation during insertion. For example, the device shown in FIG. 3 includes radial asymmetries (notably, the rectangular shape) along the longitudinal axis that maintains the device in the proper orientation following insertion. For example, in one example the spacing between proximal electrode 64 and distal electrode 66 may range from 30 millimeters (mm) to 55 mm, 35 mm to 55 mm, and from 40 mm to 55 mm and may be any range or individual spacing from 25 mm to 60 mm. In addition, ICM 10B may have a length L that ranges from 30 mm to about 70 mm. In other examples, the length L may range from 40 mm to 60 mm, 45 mm to 60 mm and may be any length or range of lengths between about 30 mm and about 70 mm. In addition, the width W of major surface 68 may range from 3 mm to 10 mm and may be any single or range of widths between 3 mm and 10 mm. The thickness of depth D of ICM 10B may range from 2 mm to 9 mm. In other examples, the depth D of ICM 10B may range from 2 mm to 5 mm and may be any single or range of depths from 2 mm to 9 mm. In addition, ICM 10B according to an example of the present disclosure is has a geometry and size designed for ease of implant and patient comfort. Examples of ICM 10B described in this disclosure may have a volume of three cubic centimeters (cm) or less, 1.5 cubic cm or less or any volume between three and 1.5 cubic centimeters.

In the example shown in FIG. 3, once inserted within patient 14B, the first major surface 68 faces outward, toward the skin of patient 14B while the second major surface 70 is located opposite the first major surface 68. In addition, in the example shown in FIG. 3, proximal end 72 and distal end 74 are rounded to reduce discomfort and irritation to surrounding tissue once inserted under the skin of patient 14B.

Proximal electrode 64 and distal electrode 66 are used to sense cardiac signals, e.g. ECG signals, intra-thoracically or extra-thoracically, which may be sub-muscularly or subcutaneously. ECG signals may be stored in a memory of the ICM 10B, and ECG data may be transmitted via integrated antenna 82 to another medical device, which may be another implantable device or an external device, such as external device 30B. In some example, electrodes 64 and 66 may additionally or alternatively be used for sensing any biopotential signal of interest, which may be, for example, an EGM, EEG, EMG, or a nerve signal, from any implanted location.

In the example shown in FIG. 3, proximal electrode 64 is in close proximity to the proximal end 72 and distal electrode 66 is in close proximity to distal end 74. In this example, distal electrode 66 is not limited to a flattened, outward facing surface, but may extend from first major surface 68 around rounded edges 76 and/or end surface 78 and onto the second major surface 70 so that the electrode 66 has a three-dimensional curved configuration. In the example shown in FIG. 3, proximal electrode 64 is located on first major surface 68 and is substantially flat, outward facing. However, in other examples proximal electrode 64 may utilize the three-dimensional curved configuration of distal electrode 66, providing a three-dimensional proximal electrode (not shown in this example). Similarly, in other examples distal electrode 66 may utilize a substantially flat, outward facing electrode located on first major surface 68 similar to that shown with respect to proximal electrode 64.

The various electrode configurations allow for configurations in which proximal electrode 64 and distal electrode 66 are located on both first major surface 68 and second major surface 70. In other configurations, such as that shown in FIG. 3, only one of proximal electrode 64 and distal electrode 66 is located on both major surfaces 68 and 70, and in still other configurations both proximal electrode 64 and distal electrode 66 are located on one of the first major surface 68 or the second major surface 70 (i.e., proximal electrode 64 located on first major surface 68 while distal electrode 66 is located on second major surface 70). In another example, ICM 10B may include electrodes on both major surface 68 and 70 at or near the proximal and distal ends of the device, such that a total of four electrodes are included on ICM 10B. Electrodes 64 and 66 may be formed of a plurality of different types of biocompatible conductive material, e.g., stainless steel, titanium, platinum, iridium, or alloys thereof, and may utilize one or more coatings such as titanium nitride or fractal titanium nitride.

In the example shown in FIG. 3, proximal end 72 includes a header assembly 80 that includes one or more of proximal electrode 64, integrated antenna 82, anti-migration projections 84, and/or suture hole 86. Integrated antenna 82 is located on the same major surface (i.e., first major surface 68) as proximal electrode 64 and is also included as part of header assembly 80. Integrated antenna 82 allows ICM 10B to transmit and/or receive data. In other examples, integrated antenna 82 may be formed on the opposite major surface as proximal electrode 64, or may be incorporated within housing 62 of ICM 10B. In the example shown in FIG. 3, anti-migration projections 84 are located adjacent to integrated antenna 82 and protrude away from first major surface 68 to prevent longitudinal movement of the device. In the example shown in FIG. 3, anti-migration projections 84 includes a plurality (e.g., nine) small bumps or protrusions extending away from first major surface 68. As discussed above, in other examples anti-migration projections 84 may be located on the opposite major surface as proximal electrode 64 and/or integrated antenna 82. In addition, in the example shown in FIG. 3 header assembly 80 includes suture hole 86, which provides another means of securing ICM 10B to patient 14B to prevent movement following insert. In the example shown, suture hole 86 is located adjacent to proximal electrode 64. In one example, header assembly 80 is a molded header assembly made from a polymeric or plastic material, which may be integrated or separable from the main portion of ICM 10B.

Figure 4A:
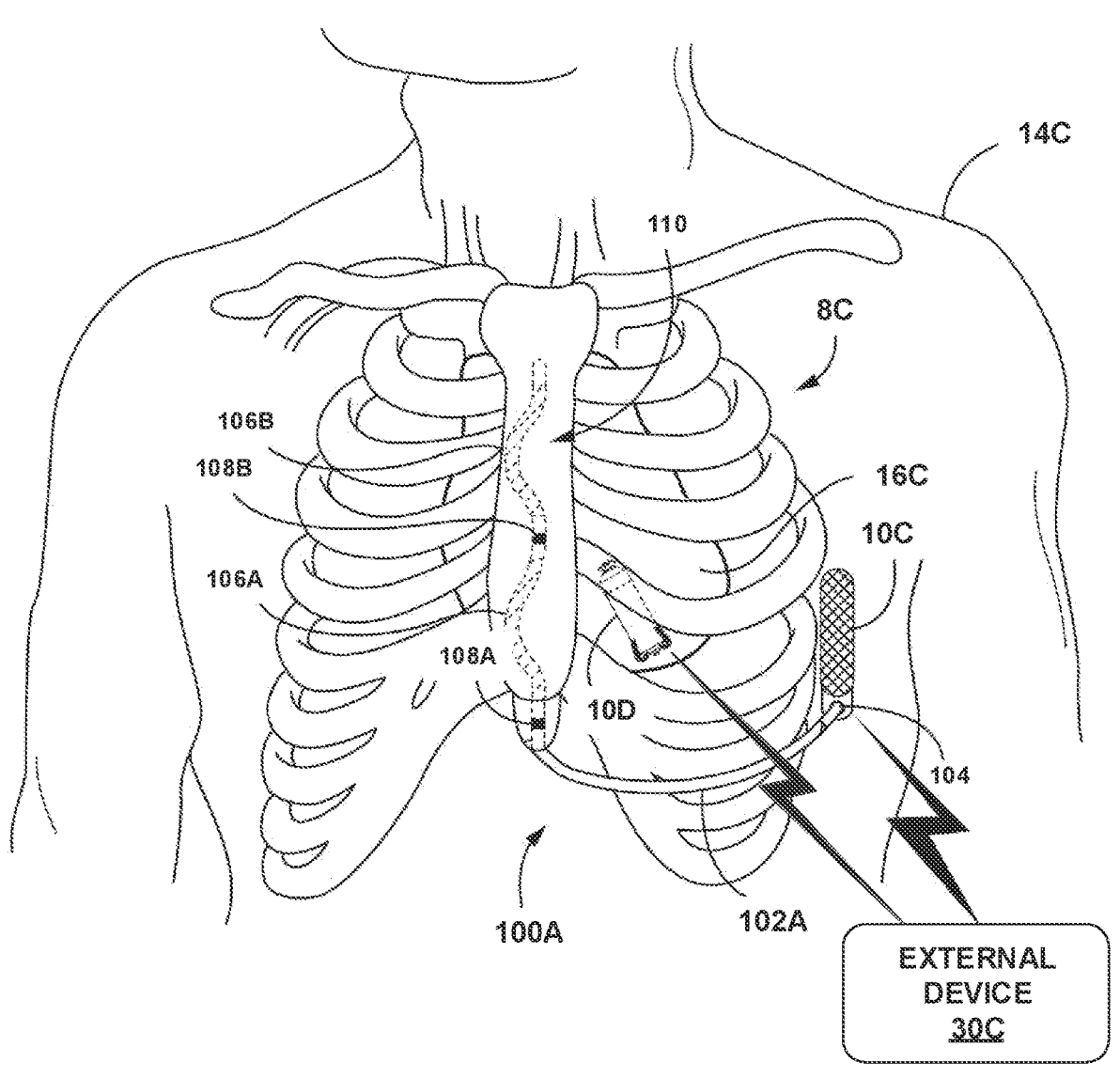
FIGS. 4A-4C is a front-view, side-view, and top-view conceptual drawings, respectively, illustrating another example medical device system in conjunction with a patient.
Figure 4B:
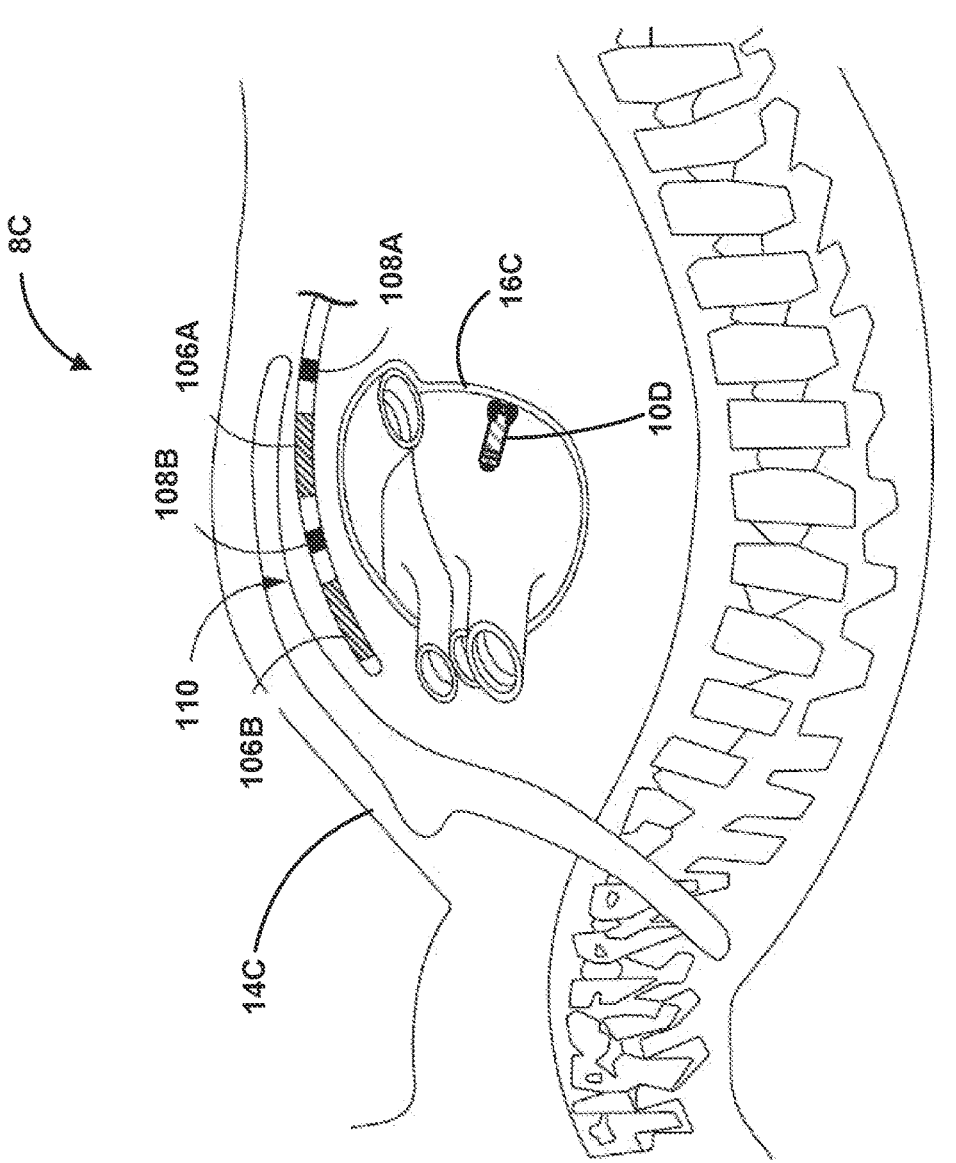
Figure 4C:
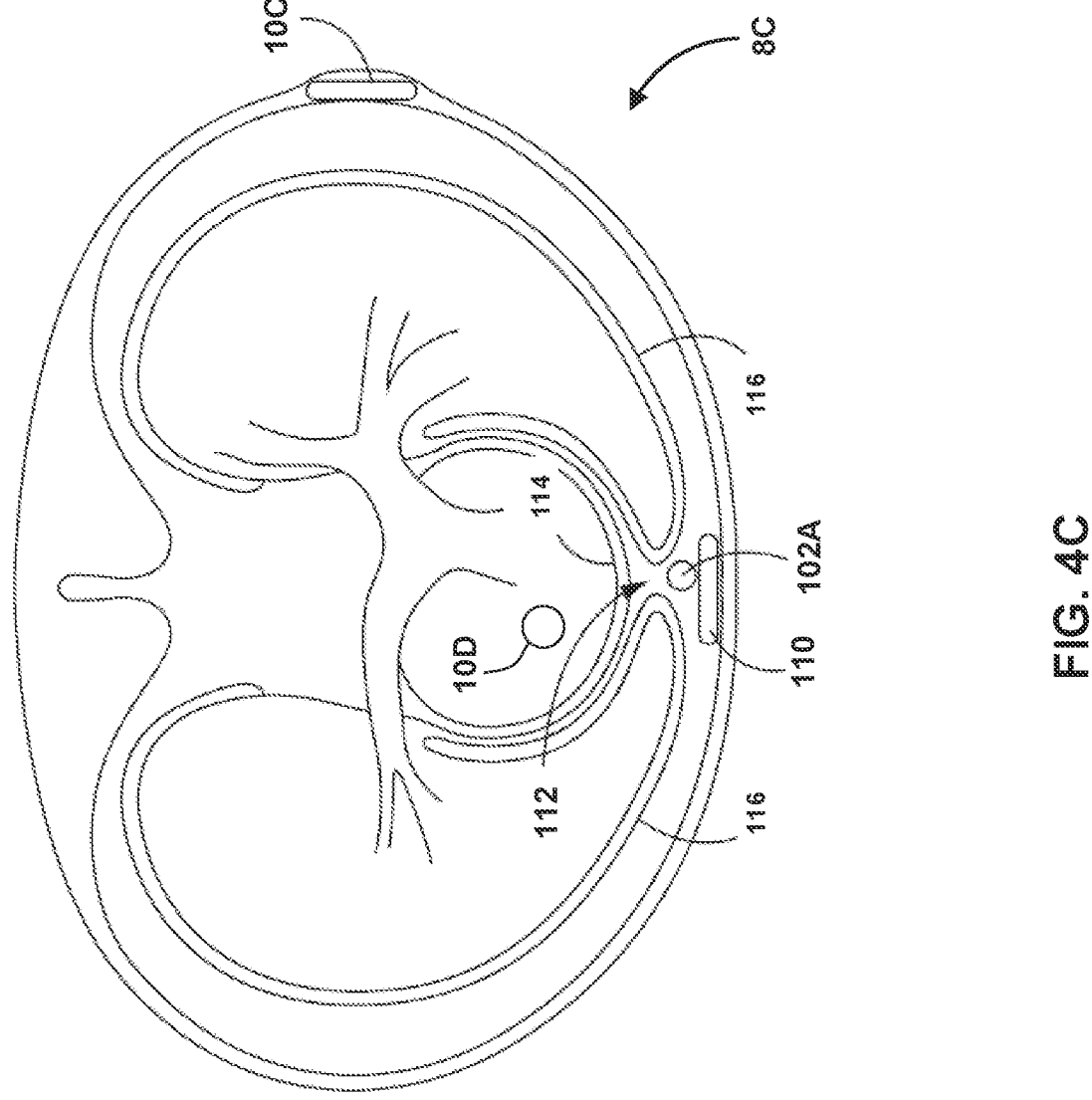

FIGS. 4A-4C are front-view, side-view, and top-view conceptual drawings, respectively, illustrating another example medical device system 8C in conjunction with a patient 14C. Medical device system 8C is another example of a medical device system configured to implement the one or more techniques described herein for determining a risk of falling based on a determination of when a person is walking and a determination of when a person is talking.

In the illustrated example, medical device system 8C includes an extracardiovascular ICD system 100A implanted within a patient 14C. ICD system 100A includes an IMD 10C, which is an ICD and is referred to hereafter as ICD 10C, connected to at least one implantable cardiac defibrillation lead 102A. ICD 10C is configured to deliver high-energy cardioversion or defibrillation pulses to a heart 16C of patient 14C when atrial or ventricular fibrillation is detected. Cardioversion shocks are typically delivered in synchrony with a detected R-wave when fibrillation detection criteria are met. Defibrillation shocks are typically delivered when fibrillation criteria are met, and the R-wave cannot be discerned from signals sensed by ICD 10C.

ICD 10C is implanted subcutaneously or submuscularly on the left side of patient 14C above the ribcage. Defibrillation lead 102A may be implanted at least partially in a substernal location, e.g., between the ribcage and/or sternum 110 and heart 16C. In one such configuration, a proximal portion of lead 102A extends subcutaneously from ICD 10C toward sternum 110 and a distal portion of lead 102A extends superior under or below the sternum 110 in the anterior mediastinum 112 (FIG. 4C). The anterior mediastinum 112 is bounded laterally by the pleurae 116 (FIG. 1C), posteriorly by the pericardium 114 (FIG. 4C), and anteriorly by the sternum 110. In some instances, the anterior wall of the anterior mediastinum may also be formed by the transversus thoracis and one or more costal cartilages. The anterior mediastinum includes a quantity of loose connective tissue (such as areolar tissue), some lymph vessels, lymph glands, substernal musculature (e.g., transverse thoracic muscle), branches of the internal thoracic artery, and the internal thoracic vein. In one example, the distal portion of lead 102A extends along the posterior side of the sternum 110 substantially within the loose connective tissue and/or substernal musculature of the anterior mediastinum. Lead 102A may be at least partially implanted in other intrathoracic locations, e.g., other non-vascular, extra-pericardial locations, including the gap, tissue, or other anatomical features around the perimeter of and adjacent to, but not attached to, the pericardium or other portion of the heart and not above the sternum 110 or ribcage.

In other examples, lead 102A may be implanted at other extracardiovascular locations. For example, defibrillation lead 102A may extend subcutaneously above the ribcage from ICD 10C toward a center of the torso of patient 14C, bend or turn near the center of the torso, and extend subcutaneously superior above the ribcage and/or sternum 110. Defibrillation lead 102A may be offset laterally to the left or the right of the sternum 110 or located over the sternum 110. Defibrillation lead 102A may extend substantially parallel to the sternum 110 or be angled lateral from the sternum 110 at either the proximal or distal end.

Defibrillation lead 102A includes an insulative lead body having a proximal end that includes a connector 104 configured to be connected to ICD 10C and a distal portion that includes one or more electrodes. Defibrillation lead 102A also includes one or more conductors that form an electrically conductive path within the lead body and interconnect the electrical connector and respective ones of the electrodes.

Defibrillation lead 102A includes a defibrillation electrode that includes two sections or segments 106A and 106B, collectively (or alternatively) defibrillation electrode 106. The defibrillation electrode 106 is toward the distal portion of defibrillation lead 102A, e.g., toward the portion of defibrillation lead 102A extending along the sternum 110. Defibrillation lead 102A is placed below and/or along sternum 110 such that a therapy vector between segments 106A or 106B and a housing electrode formed by or on ICD 10C (or other second electrode of the therapy vector) is substantially across a ventricle of heart 16C. The therapy vector may, in one example, be viewed as a line that extends from a point on defibrillation electrode 106 (e.g., a center of one of the segments 106A or 106B) to a point on the housing electrode of ICD 10C. Defibrillation electrode 106 may, in one example, be an elongated coil electrode.

Defibrillation lead 102A may also include one or more sensing electrodes, such as sensing electrodes 108A and 108B (individually or collectively, "sensing electrode(s) 108"), located along the distal portion of defibrillation lead 102A. In the example illustrated in FIG. 4A and FIG. 4B, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102A may include more or fewer electrodes at various locations proximal and/or distal to defibrillation electrode 106. In the same or different examples, ICD 10C may include one or more electrodes on another lead (not shown).

ICD system 100A may sense electrical signals via one or more sensing vectors that include combinations of electrodes 108A and 108B and the housing electrode of ICD 10C. In some instances, ICD 10C may sense cardiac electrical signals using a sensing vector that includes one of the segments 106A and 106B and one of sensing electrodes 108A and 108B or the housing electrode of ICD 9. The sensed electrical intrinsic signals may include electrical signals generated by cardiac muscle and indicative of depolarizations and repolarizations of heart 16C at various times during the cardiac cycle. ICD 10C analyzes the electrical signals sensed by the one or more sensing vectors to detect tachyarrhythmia, such as ventricular tachycardia or ventricular fibrillation. In response to detecting the tachyarrhythmia, ICD 10C may begin to charge a storage element, such as a bank of one or more capacitors, and, when charged, deliver one or more defibrillation pulses via defibrillation electrode 106 of defibrillation lead 102A if the tachyarrhythmia is still present.

Medical device system 8C also includes an IMD 10D, which is implanted within heart 16C and configured to deliver cardiac pacing to the heart, e.g., is an intracardiac pacing device (IPD). IMD 10D is referred to as IPD 10D hereafter. In the illustrated example, IPD 10D is implanted within the right ventricle of heart 16C. However, in other examples, system 8C may additionally or alternatively include one or more IPDs 10D within other chambers of heart 16C, or similarly configured pacing devices attached to an external surface of heart 16C (e.g., in contact with the epicardium) such that the pacing device is disposed outside of heart 16C.

IPD 10D is configured to sense electrical activity of heart 16C and deliver pacing therapy, e.g., bradycardia pacing therapy, cardiac resynchronization therapy (CRT), anti-tachycardia pacing (ATP) therapy, and/or post-shock pacing, to heart 16C. IPD 10D may be attached to an interior wall of heart 16C via one or more fixation elements that penetrate the tissue. These fixation elements may secure IPD 10D to the cardiac tissue and retain an electrode (e.g., a cathode or an anode) in contact with the cardiac tissue.

IPD 10D may be capable sensing electrical signals using the electrodes carried on the housing of IPD 10D. These electrical signals may be electrical signals generated by cardiac muscle and indicative of depolarizations and repolarizations of heart 16C at various times during the cardiac cycle. IPD 10D may analyze the sensed electrical signals to detect bradycardia and tachyarrhythmias, such as ventricular tachycardia or ventricular fibrillation. In response to detecting bradycardia, IPD 10D may deliver bradycardia pacing via the electrodes of IPD 10D. In response to detecting tachyarrhythmia, IPD 10D may, e.g., depending on the type of tachyarrhythmia, deliver ATP therapy via the electrodes of IPD 10D. In some examples, IPD 10D may deliver post-shock pacing in response to determining that another medical device, e.g., ICD 10C, delivered an anti-tachyarrhythmia shock.

IPD 10D and ICD 10C may be configured to coordinate their arrhythmia detection and treatment activities. In some examples IPD 10D and ICD 10C may be configured to operate completely independently of one another. In such a case, IPD 10D and ICD 10C are not capable of establishing telemetry communication sessions with one another to exchange information about sensing and/or therapy using one-way or two-way communication. Instead, each of IPD 10D and ICD 10C analyze the data sensed via their respective electrodes to make tachyarrhythmia detection and/or therapy decisions. As such, each device does not know if the other will detect the tachyarrhythmia, if or when it will provide therapy, and the like. In some examples, IPD 10D may be configured to detect anti-tachyarrhythmia shocks delivered by ICD system 100A, which may improve the coordination of therapy between subcutaneous ICD 10C and IPD 10D without requiring device-to-device communication. In this manner, IPD 10D may coordinate the delivery of cardiac stimulation therapy, including the termination of ATP and the initiation of the delivery of post-shock pacing, with the application of an anti-tachyarrhythmia shock merely through the detection of defibrillation pulses and without the need to communicate with the defibrillation device applying the anti-tachyarrhythmia shock.

In other examples, IPD 10D and ICD 10C may engage in communication to facilitate the appropriate detection of arrhythmias and/or delivery of therapy. The communication may include one-way communication in which one device is configured to transmit communication messages and the other device is configured to receive those messages. The communication may instead include two-way communication in which each device is configured to transmit and receive communication messages.

External device 30C may be configured substantially similarly to external device 30A described above with respect to FIG. 1. External device 30C may be configured to communicate with one or both of ICD 10C and IPD 10D. In examples where external device 30C only communicates with one of ICD 10C and IPD 10D, the non-communicative device may receive instructions from or transmit data to the device in communication with external device 30C. In some examples, a user may interact with device 30C remotely via a networked computing device. The user may interact with external device 30C to communicate with IPD 10D and/or ICD 10C.

For example, the user may interact with external device 30C to send an interrogation request and retrieve sensed physiological data (such as when a person was walking, when a person was talking, or a risk of falling) or therapy delivery data stored by one or both of ICD 10C and IPD 10D, and program or update therapy parameters that define therapy, or perform any other activities with respect to ICD 10C and IPD 10D. Although the user is a physician, technician, surgeon, electrophysiologist, or other healthcare professional, the user may be patient 14C in some examples. For example, external device 30C may allow a user to program any coefficients, weighting factors, or techniques for determining a risk of falling. As another example, external device 30C may be used to program commands or operating parameters into ICD 10C for controlling its functioning. External device 30C may be used to interrogate ICD 10C to retrieve data, including device operational data as well as physiological data accumulated in IMD memory, such as data associated with when a person is walking, when a person is talking, or a risk of falling based on the determination of when the person is walking and when the person is talking. ICD 10C may be configured to implement the various features or aspects of the present disclosure for determining when a person is walking, when a person is talking, and/or a risk of falling.

Medical device system 8C is an example of a medical device system configured to determine a risk of falling based on a determination of when a person is walking and a determination of when a person is talking. Such techniques as contemplated may be performed by processing circuitry of medical device system 8C, such as processing circuitry of one or both of ICD 10C and external device 30C, individually, or collectively, as discussed in further detail below following a description provided in connection with FIG. 10. Other example medical device systems that may be configured to implement the techniques are described herein.

Figure 5:
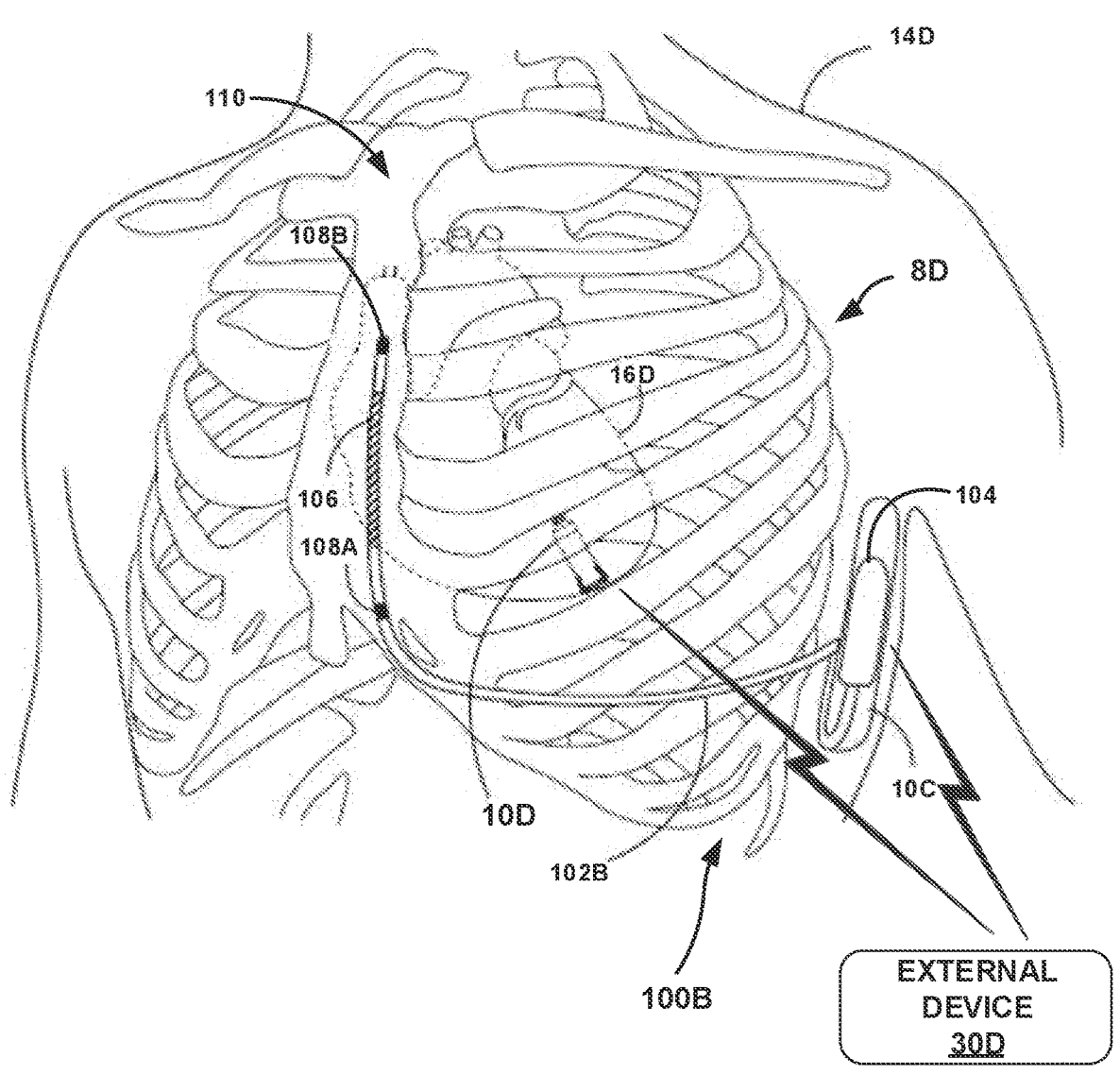
FIG. 5 is a conceptual drawing illustrating another example medical device system in conjunction with a patient.

FIG. 5 is a conceptual drawing illustrating another example medical device system 8D that includes an extra-cardiovascular ICD system 100B and IPD 10D implanted within a person. Medical device system 8D may be configured to perform any of the techniques described herein with respect to medical device system 8C of FIGS. 4A-4C. Components with like numbers in FIGS. 4A-4C and FIG. 5 may be similarly configured and provide similar functionality.

In the example of FIG. 5, extracardiovascular ICD system 100B includes ICD 10C coupled to a defibrillation lead 102B. Unlike defibrillation lead 102A of FIGS. 4A—4C, defibrillation lead 102B extends subcutaneously above the ribcage from ICD 10C. In the illustrated example, defibrillation lead 102B extends toward a center of the torso of patient 14D, bends or turns near the center of the torso, and extends subcutaneously superior above the ribcage and/or sternum 110. Defibrillation lead 102B may be offset laterally to the left or the right of sternum 110 or located over sternum 110. Defibrillation lead 102B may extend substantially parallel to sternum 102 or be angled lateral from the sternum at either the proximal or distal end.

Defibrillation lead 102B includes an insulative lead body having a proximal end that includes a connector 104 configured to be connected to ICD 10C and a distal portion that includes one or more electrodes. Defibrillation lead 102B also includes one or more conductors that form an electrically conductive path within the lead body and interconnect the electrical connector and respective ones of the electrodes. In the illustrated example, defibrillation lead 102B includes a single defibrillation electrode 106 toward the distal portion of defibrillation lead 102B, e.g., toward the portion of defibrillation lead 102B extending along sternum 110. Defibrillation lead 102B is placed along sternum 110 such that a therapy vector between defibrillation electrode 106 and a housing electrode formed by or on ICD 10C (or other second electrode of the therapy vector) is substantially across a ventricle of heart 16D.

Defibrillation lead 102B may also include one or more sensing electrodes, such as sensing electrodes 108A and 108B, located along the distal portion of defibrillation lead 102B. In the example illustrated in FIG. 5, sensing electrodes 108A and 108B are separated from one another by defibrillation electrode 106. In other examples, however, sensing electrodes 108A and 108B may be both distal of defibrillation electrode 106 or both proximal of defibrillation electrode 106. In other examples, lead 102B may include more or fewer electrodes at various locations proximal and/or distal to defibrillation electrode 106, and lead 102B may include multiple defibrillation electrodes, e.g., segments 106A and 106B as illustrated in the example of FIGS. 4A-4C.

Medical device system 8D is an example of a medical device system configured to determine a risk of falling based on a determination of when a person is walking and a determination of when a person is talking. Such techniques as contemplated may be performed by processing circuitry of medical device system 8D, such as processing circuitry of one or both of ICD 10C and external device 30D, individually, or collectively, as discussed in further detail below.

Figure 6:
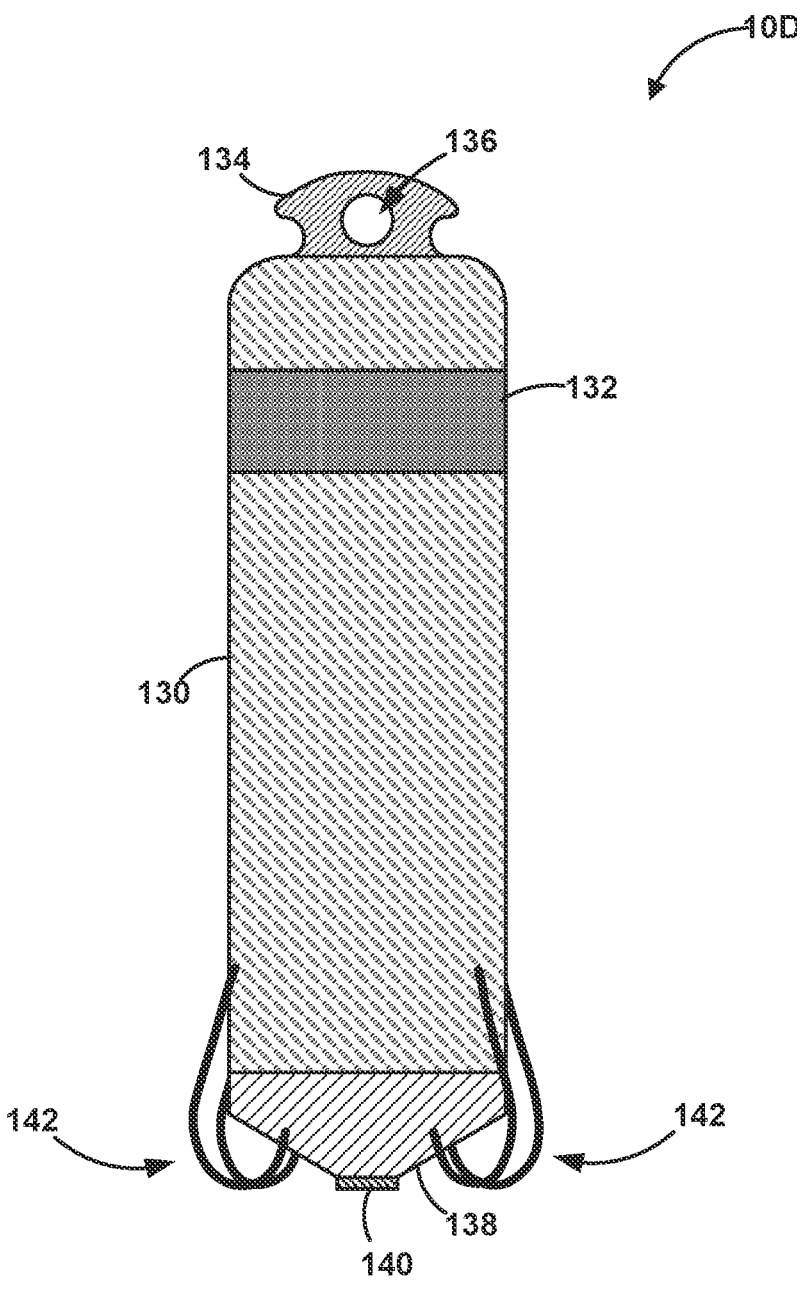
FIG. 6 is a conceptual diagram illustrating an example configuration of the intracardiac pacing device of FIGS. 4A-5.

FIG. 6 is a conceptual drawing illustrating an example configuration of IPD 10D. As shown in FIG. 6, IPD 10D includes case 130, cap 138, electrode 140, electrode 132, fixation mechanisms 142, flange 134, and opening 136. Together, case 130 and cap 138 may be considered the housing of IPD 10D. In this manner, case 130 and cap 138 may enclose and protect the various electrical components, e.g., circuitry, within IPD 10D. Case 130 may enclose substantially all of the electrical components, and cap 138 may seal case 130 and create the hermetically sealed housing of IPD 10D. Although IPD 10D is generally described as including one or more electrodes, IPD 10D may typically include at least two electrodes (e.g., electrodes 132 and 140) to deliver an electrical signal (e.g., therapy such as cardiac pacing) and/or provide at least one sensing vector.

Electrodes 132 and 140 are carried on the housing created by case 130 and cap 138. In this manner, electrodes 132 and 140 may be considered leadless electrodes. In the example of FIG. 6, electrode 140 is disposed on the exterior surface of cap 138. Electrode 140 may be a circular electrode positioned to contact cardiac tissue upon implantation. Electrode 132 may be a ring or cylindrical electrode disposed on the exterior surface of case 130. Both case 130 and cap 138 may be electrically insulating.

Electrode 140 may be used as a cathode and electrode 132 may be used as an anode, or vice versa, for delivering cardiac pacing such as bradycardia pacing, CRT, ATP, or post-shock pacing. However, electrodes 132 and 140 may be used in any stimulation configuration. In addition, electrodes 132 and 140 may be used to detect intrinsic electrical signals from cardiac muscle.

Fixation mechanisms 142 may attach IPD 10D to cardiac tissue. Fixation mechanisms 142 may be active fixation tines, screws, clamps, adhesive members, or any other mechanisms for attaching a device to tissue. As shown in the example of FIG. 6, fixation mechanisms 142 may be constructed of a memory material, such as a shape memory alloy (e.g., nickel titanium), that retains a preformed shape. During implantation, fixation mechanisms 142 may be flexed forward to pierce tissue and allowed to flex back towards case 130. In this manner, fixation mechanisms 142 may be embedded within the target tissue.

Flange 144 may be provided on one end of case 130 to enable tethering or extraction of IPD 10D. For example, a suture or other device may be inserted around flange 144 and/or through opening 146 and attached to tissue. In this manner, flange 144 may provide a secondary attachment structure to tether or retain IPD 10D within heart 16C (or 16D) if fixation mechanisms 142 fail. Flange 144 and/or opening 146 may also be used to extract IPD 10D once the IPD needs to be explanted (or removed) from patient 14D if such action is deemed necessary.

Referring back to FIGS. 4A-5, medical device systems 8C and 8D are examples of medical device systems configured to determine a risk of falling based on a determination of when a person is walking and a determination of when a person is talking. Such techniques may be performed by processing circuitry of medical device system 8C or 8D, such as processing circuitry of one or more of ICD 10C, IPD 10D, and external device 30C or 30D, individually, or collectively. Although the example medical devices systems 8C and 8D of FIGS. 4A-5 are illustrated as including both ICD 10C and IPD 10D, other examples may include only one of ICD 10C or IPD 10D, alone, or in combination with other implanted or external devices.

Figure 7:
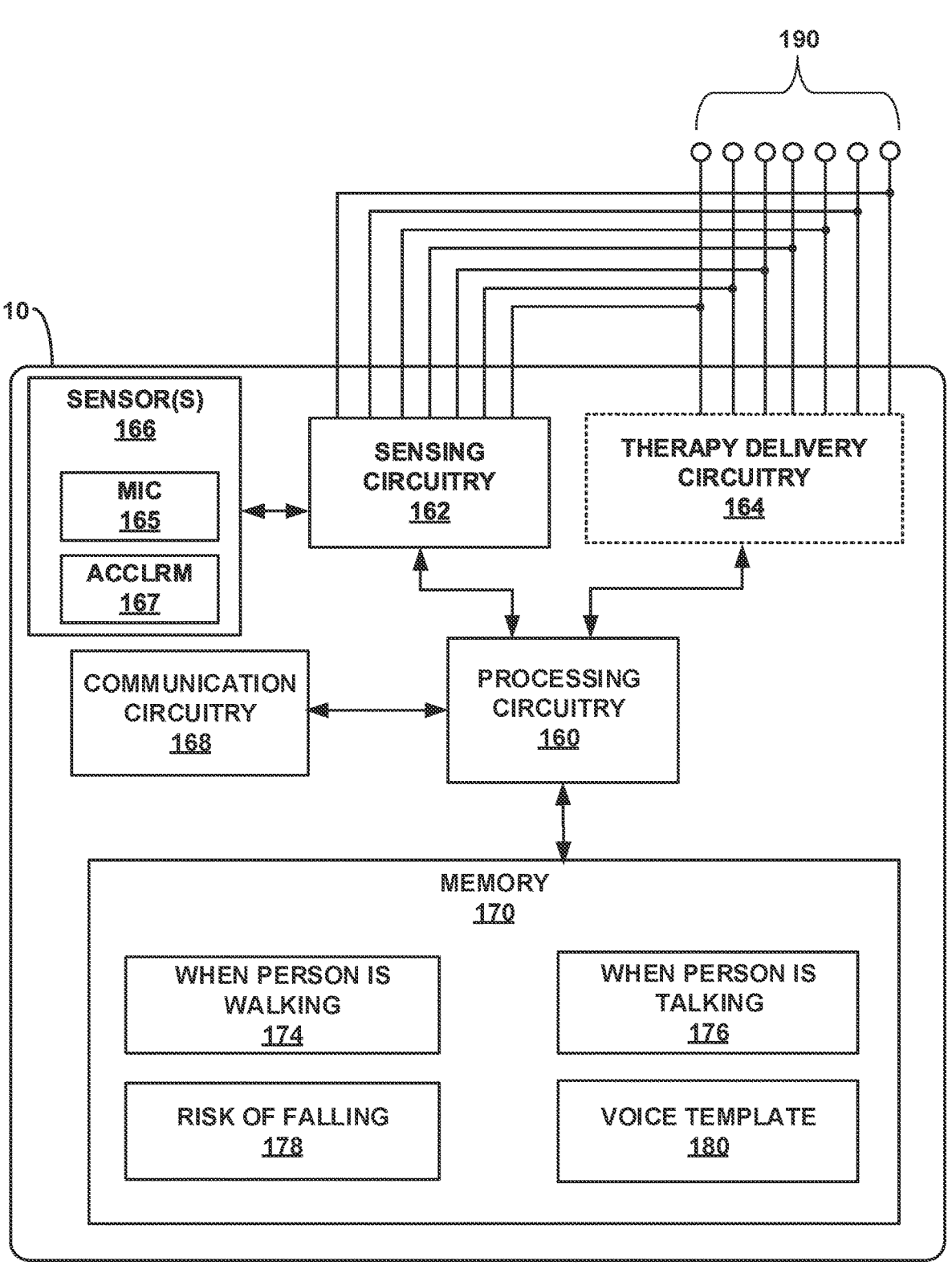
FIG. 7 is a functional block diagram illustrating an example configuration of an implantable medical device.

FIG. 7 is a functional block diagram illustrating an example configuration of an IMD 10. IMD 10 may correspond to any of ICD 10A, ICM 10B, ICD 10C, IPD 10D, or another IMD configured to implement techniques for determining a risk of falling based on a determination of when a person is walking and a determination of when a person is talking as described in this disclosure. IMD 10 may implement the techniques for any of patients 14A-14D (hereinafter patient 14) having hearts 16A-16D (hereinafter heart 16). In the illustrated example, IMD 10 includes processing circuitry 160 and an associated memory 170, sensing circuitry 162, therapy delivery circuitry 164, sensors 166, and communication circuitry 168. However, ICD 10A, ICM 10B, ICD 10C, and IPD 10D need not include all of these components, or may include additional components. For example, ICM 10B may not include therapy delivery circuitry 164, in some examples (illustrated by intermittent line).

Memory 170 includes computer-readable instructions that, when executed by processing circuitry 160, cause IMD 10 and processing circuitry 160 to perform various functions attributed to IMD 10 and processing circuitry 160 herein (e.g., determine when a person is walking, determine when a person is talking, and/or determine a risk of falling). Memory 170 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processing circuitry 160 may include fixed function circuitry and/or programmable processing circuitry. Processing circuitry 160 may include any one or more of a microprocessor, a controller, a digital signal processor (DSP), an application specific integrated circuit (ASIC), a field-programmable gate array (FPGA), or equivalent discrete or analog logic circuitry. In some examples, processing circuitry 160 may include multiple components, such as any combination of one or more microprocessors, one or more controllers, one or more DSPs, one or more ASICs, or one or more FPGAs, as well as other discrete or integrated logic circuitry. The functions attributed to processing circuitry 160 herein may be embodied as software, firmware, hardware or any combination thereof. Processing circuitry 160 may be communicatively coupled elements of IMD 10 such as memory 170, accelerometry circuitry (ACCLRM) 167, and microphone (MIC) 165.

Sensing circuitry 162 and therapy delivery circuitry 164 may be coupled to electrodes 190. Electrodes 190 illustrated in FIG. 7 may correspond to, for example: electrodes 12, 22, 24, 26, 28, 44, and 44 of ICD 10A (FIG. 1); electrodes 64 and 66 of ICM 10B (FIG. 3); electrodes 106, 108, and one or more housing electrodes of ICD 10C (FIGS. 4A-5); or electrodes 132 and 140 of IPD 10D (FIG. 6).

Sensing circuitry 162 monitors signals from a selected two or more of electrodes 190 in order to monitor electrical activity of heart 16, impedance, or other electrical phenomenon. Sensing of a cardiac electrical signal may be done to determine heart rates or heart rate variability, or to detect arrhythmias (e.g., tachyarrhythmias or bradycardia) or other electrical signals. In some examples, sensing circuitry 162 may include one or more filters and amplifiers for filtering and amplifying a signal received from electrodes 190.

The resulting cardiac electrical signal may be passed to cardiac event detection circuitry that detects a cardiac event when the cardiac electrical signal crosses a sensing threshold. The cardiac event detection circuitry may include a rectifier, filter and/or amplifier, a sense amplifier, comparator, and/or analog-to-digital converter. Sensing circuitry 162 outputs an indication to processing circuitry 160 in response to sensing of a cardiac event (e.g., detected P-waves or R-waves).

In this manner, processing circuitry 160 may receive detected cardiac event signals corresponding to the occurrence of detected R-waves and P-waves in the respective chambers of heart 16. Indications of detected R-waves and P-waves may be used for detecting ventricular and/or atrial tachyarrhythmia episodes, e.g., ventricular or atrial fibrillation episodes. Some detection channels may be configured to detect cardiac events, such as P- or R-waves, and provide indications of the occurrences of such events to processing circuitry 160.

Sensing circuitry 162 may also include a switch module to select which of the available electrodes 190 (or electrode polarities) are used to sense the heart activity. In examples with several electrodes 190, processing circuitry 160 may select the electrodes that function as sense electrodes, i.e., select the sensing configuration, via the switch module within sensing circuitry 162. Sensing circuitry 162 may also pass one or more digitized EGM signals to processing circuitry 160 for analysis, e.g., for use in cardiac rhythm discrimination.

Processing circuitry 160 may implement programmable counters. If IMD 10 is configured to generate and deliver pacing pulses to heart 16, such counters may control the basic time intervals associated with bradycardia pacing (e.g., DDD, VVI, DVI, VDD, AAI, DDI, DDDR, VVIR, DVIR, VDDR, AAIR, DDIR pacing) and other modes of pacing. Intervals defined by processing circuitry 160 may include atrial and ventricular pacing escape intervals, refractory periods during which sensed P-waves and R-waves are ineffective to restart timing of the escape intervals, and the pulse widths of the pacing pulses. The durations of these intervals may be determined by processing circuitry 160 in response to pacing mode parameters stored in memory 170.

Interval counters implemented by processing circuitry 160 may be reset upon sensing of R-waves and P-waves with detection channels of sensing circuitry 162, or upon the generation of pacing pulses by therapy delivery circuitry 164, and thereby control the basic timing of cardiac pacing functions, including bradycardia pacing, CRT, ATP, or post-shock pacing. The value of the count present in the interval counters when reset by sensed R-waves and P-waves may be used by processing circuitry 160 to measure the durations of R-R intervals, P-P intervals, P-R intervals and R-P intervals, which are measurements that may be stored in memory 170. Processing circuitry 160 may use the count in the interval counters to detect a tachyarrhythmia event, such as atrial fibrillation (AF), atrial tachycardia (AT), VF, or VT. These intervals may also be used to detect the overall heart rate, ventricular contraction rate, and heart rate variability. A portion of memory 170 may be configured as a plurality of recirculating buffers, capable of holding series of measured intervals, which may be analyzed by processing circuitry 160 in response to the occurrence of a pace or sense interrupt to determine whether the heart 16 of patient 14 is presently exhibiting atrial or ventricular tachyarrhythmia.

In some examples, processing circuitry 160 may determine that tachyarrhythmia has occurred by identification of shortened R-R (or P-P) interval lengths. Generally, processing circuitry 160 detects tachycardia when the interval length falls below 220 milliseconds and fibrillation when the interval length falls below 180 milliseconds. In other examples, processing circuitry 160 may detect ventricular tachycardia when the interval length falls between 330 milliseconds and ventricular fibrillation when the interval length falls below 240 milliseconds. These interval lengths are merely examples, and a user may define the interval lengths as desired, which may then be stored within memory 170. This interval length may need to be detected for a certain number of consecutive cycles, for a certain percentage of cycles within a running window, or a running average for a certain number of cardiac cycles, as examples. In other examples, additional patient parameters may be used to detect an arrhythmia. For example, processing circuitry 160 may analyze one or more morphology measurements, impedances, or any other physiological measurements to determine that patient 14 is experiencing a tachyarrhythmia.

In addition to detecting and identifying specific types of cardiac events, e.g., cardiac depolarizations, sensing circuitry 162 may also sample the detected intrinsic signals to generate an electrogram or other time-based indication of cardiac events. Sensing circuitry 162 may include an analog-to-digital converter or other circuitry configured to sample and digitize the electrical signal sensed via electrodes 190. Processing circuitry 160 may analyze the digitized signal for a variety of purposes, including morphological identification or confirmation of tachyarrhythmia of heart 16. As another example, processing circuitry 160 may analyze the digitized cardiac electrogram signal to identify and measure a variety of morphological features of the signal.

In some examples, sensing circuitry 162 is configured to sense other physiological signals of patient 14. For example, sensing circuitry 162 may be configured to sense signals that vary with changing thoracic impedance of patient 14. The thoracic impedance may vary based on fluid volume or edema in patient 14.

Sensing circuitry 162 may use any two or more of electrodes 190 to sense thoracic impedance. As the tissues within the thoracic cavity of patient 14 change in fluid content, the impedance between two electrodes may also change. For example, the impedance between a defibrillation coil electrode (42, 44, 106) and the housing electrode may be used to monitor changing thoracic impedance.

In some examples, processing circuitry 160 measured thoracic impedance values to determine a fluid index. As more fluid is retained within patient 14, e.g., edema increases, and the thoracic impedance decreases or remains relatively high, the fluid index increases. Conversely, as the thoracic impedance increases or remains relatively low, the fluid index decreases.

The thoracic impedance may also vary with patient respiration. In some examples, processing circuitry 160 may determine values of one or more respiration-related patient parameters based on thoracic impedance sensed by sensing circuitry 162. Respiration-related patient parameters may include, as examples, respiration rate, respiration depth, or the occurrence or magnitude of dyspnea or apneas.

The magnitude of the cardiac electrogram may also vary based on patient respiration, e.g., generally at a lower frequency than the cardiac cycle. In some examples, processing circuitry 160 and/or sensing circuitry 162 may filter the cardiac electrogram to emphasize the respiration component of the signal. Processing circuitry 160 may analyze the filtered cardiac electrogram signal to determine values of respiration-related patient parameters.

In the example of FIG. 7, IMD 10 includes sensors 166 coupled to sensing circuitry 162. Although illustrated in FIG. 7 as included within IMD 10, sensors 166 may be external to IMD 10, e.g., coupled to IMD 10 via one or more leads, or configured to wirelessly communicate with IMD 10. In some examples, sensors 166 transduce a signal indicative of a patient parameter, which may be amplified, filtered, or otherwise processed by sensing circuitry 162. In such examples, processing circuitry 160 determines values of patient parameters based on the signals. In some examples, sensors 166 determine the patient parameter values, and communicate them, e.g., via a wired or wireless connection, to processing circuitry 160.

In some examples, sensors 166 include accelerometer circuitry 167, e.g., one or more 3-axis accelerometers. Signals generated by the accelerometer circuitry 167, such as one or more of a sagittal axis signal, a vertical axis signal and a transverse axis signal, may be indicative of, as examples, gross body movement (e.g., activity) of patient 14, such as patient 14 walking, patient posture, heart sounds or other vibrations or movement associated with the beating of the heart, or coughing, rales, or other respiration abnormalities. In some examples, sensors 166 include one or more microphones (e.g., microphone 165) configured to detect heart sounds, respiration abnormalities, or to capture a voice of patient 14 and/or other sensors configured to detect patient activity or posture, such as gyroscopes and/or strain gauges. In some examples, sensors 166 may include sensors configured to transduce signals indicative of blood flow, oxygen saturation of blood, or patient temperature, and processing circuitry 160 may determine patient parameters values based on these signals.

In some examples, sensors 166 include one or more pressure sensors that transduce one or more signals indicative of blood pressure, and processing circuitry 160 determines one or more patient parameter values based on the pressure signals. Patient parameter values determined based on pressure may include, as examples, systolic or diastolic pressure values, such as pulmonary artery diastolic pressure values. In some examples, a separate pressure-sensing IMD 50 includes one or more sensors and sensing circuitry configured to generate a pressure signal, and processing circuitry 160 determines patient parameter values related to blood pressure based on information received from IMD 50.

Therapy delivery circuitry 164 is configured to generate and deliver electrical therapy to the heart. Therapy delivery circuitry 164 may include one or more pulse generators, capacitors, and/or other components capable of generating and/or storing energy to deliver as pacing therapy, defibrillation therapy, cardioversion therapy, other therapy or a combination of therapies. In some instances, therapy delivery circuitry 164 may include a first set of components configured to provide pacing therapy and a second set of components configured to provide anti-tachyarrhythmia shock therapy. In other instances, therapy delivery circuitry 164 may utilize the same set of components to provide both pacing and anti-tachyarrhythmia shock therapy. In still other instances, therapy delivery circuitry 164 may share some of the pacing and shock therapy components while using other components solely for pacing or shock delivery.

Therapy delivery circuitry 164 may include charging circuitry, one or more charge storage devices, such as one or more capacitors, and switching circuitry that controls when the capacitor(s) are discharged to electrodes 190 and the widths of pulses. Charging of capacitors to a programmed pulse amplitude and discharging of the capacitors for a programmed pulse width may be performed by therapy delivery circuitry 164 according to control signals received from processing circuitry 160, which are provided by processing circuitry 160 according to parameters stored in memory 170. Processing circuitry 160 controls therapy delivery circuitry 164 to deliver the generated therapy to the heart via one or more combinations of electrodes 190, e.g., according to parameters stored in memory 170. Therapy delivery circuitry 164 may include switch circuitry to select which of the available electrodes 190 are used to deliver the therapy, e.g., as controlled by processing circuitry 160.

In some examples, processing circuitry 160 may determine when a person is walking. Details on how to determine when a step is taken can be found in commonly-assigned U.S. patent application Ser. No. 15/603,776, titled, "STEP DETECTION USING ACCELEROMETER AXIS," filed May 24, 2017, now published as US Patent Application Publication No. US 2018/0035920 A1 and claiming the benefit of Provisional Application No. 62/370,102, filed on Aug. 2, 2016, the entire content of each of which is incorporated by reference herein. In some examples, processing circuitry 160 may determine when a person is walking by monitoring activity using thresholds which may be set for walking, such as at least 23 integrated counts during a 10 second epoch. For example, processing circuitry 160 monitor a frontal signal from accelerometer 167 to create counts. Processing circuitry 160 may sum these counts over a period of time to determine whether a patient is walking or not walking. In this manner, processing circuitry 160 may determine when the person is walking based on at least one signal from accelerometer circuitry 167. Processing circuitry 160 may store, in memory 170 (e.g., in when a person is walking 174), a start time and a stop time of the determined walking.

In some examples, processing circuitry 160 may determine when a person is talking. For example, processing circuitry 160 may store in memory 170 voice template 180. Voice template 180 may be created by processing circuitry 160 based on a voice captured by microphone 165 or may be created by processing circuitry of external device 30 based on a voice captured by a different microphone (e.g., a smart phone microphone) which may be sent by external device to processing circuitry 160 via communication circuitry 168. Processing circuitry may monitor microphone 165 for captured voices and compare captured voices to voice template 180 to determine if the captured voice matches the voice of patient 14. Processing circuitry 160 may apply a voice matching application to a captured voice to determine if the captured voice is that of patient 14, for example, using a voice biometrics algorithm (not shown), which may be stored in memory 170. In this manner, processing circuitry 160 may determine when the person is talking based on the captured voice. Processing circuitry 160 may store, in memory 170 (e.g., in when a person is talking 176), a start time and a stop time of the determined walking.

Processing circuitry 160 may determine a risk of falling based on the determination of when the person is walking and the determination of when the person is talking. Processing circuitry 160 may store the risk of falling in risk of falling 178. For example, IMD 10 may compare the times when the person is walking to the times when the person is talking and determine a risk of falling based on the comparison. For example, IMD 10 may determine the risk of falling by comparing the start time and the stop time of the determined walking to the start time and the stop time of the determined talking and determining an amount of overlap in the determined walking and the determined talking based on the comparison. In some examples, IMD 10 may determine a risk of falling based on the determined amount of overlap.

For example, if there is an overlap in the walking and talking times, IMD 10 may determine that the risk of falling is low. If there is not an overlap in the walking and talking times, IMD 10 may determine that the risk of falling is high. In some examples, rather than a low or high determination, IMD 10 may determine a risk of falling score based on a summation of the amount of overlap in the walking and talking times. For example, the risk of falling score may be on a scale of 1-5, 1-10, 1-100, or some other scale. For example, if there is complete overlap of the walking and talking times, the risk of falling may be at the low side of the scale, 1, for example. If there is no overlap of walking and talking times, the risk of falling may be at the high side of the risk of falling scale, 100, for example.

In some examples, IMD 10 may determine a risk of falling score based on the amount of overlap in the walking and talking times and the amount of walking time and/or the amount of talking time. For example, if there is an hour of walking, three hours of talking, and an overlap of walking and talking of 30 minutes, IMD 10 may determine the risk of falling to be near the low end of the risk of falling scale, 5, for example. For example, IMD 10 may allow for time for responsive talking by other individuals, as it may be unlikely that a person would speak for a long period of time without stopping their speech to listen for a response from another individual.

Communication circuitry 168 includes any suitable hardware, firmware, software or any combination thereof for communicating with another device, such as an external device 30 or another IMD or sensor. Under the control of processing circuitry 160, communication circuitry 168 may receive downlink telemetry from and send uplink telemetry to external device 30 or another device with the aid of an antenna, which may be internal and/or external. In some examples, communication circuitry 168 may communicate with a local external device, and processing circuitry 160 may communicate with a networked computing device via the local external device and a computer network, such as the Medtronic CareLink® Network developed by Medtronic, plc, of Dublin, Ireland.

A clinician or other user may retrieve data from IMD 10 using external device 30 or another local or networked computing device configured to communicate with processing circuitry 160 via communication circuitry 168. The clinician may also program parameters of IMD 10 using external device 30 or another local or networked computing device.

Figure 8:
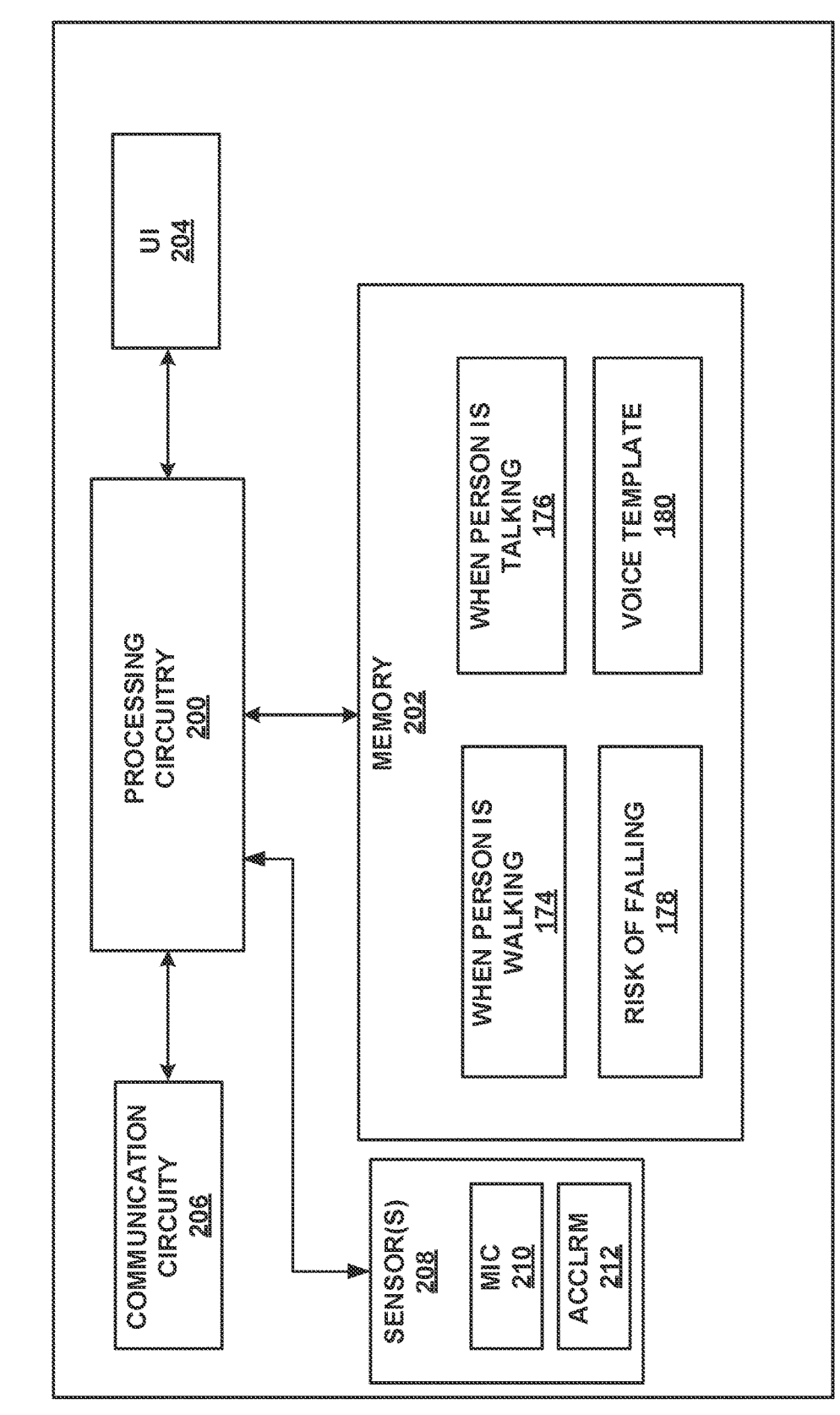
FIG. 8 is a functional block diagram illustrating an example configuration of an external device configured to communicate with one or more implantable medical devices.

FIG. 8 is a functional block diagram illustrating an example configuration of an external device 30. In some examples, external device 30 is configured to communicate with one or more IMDs 10. In some examples, external device 30 is not configured to communicate with one or more IMDs 10. In some examples, external device 30 is configured to implement the techniques of this disclosure. In some examples, external device 30 may be a smart phone or a wearable device, such as a smart watch or fitness tracker.

In the example of FIG. 8, external device 30 includes processing circuitry 200, memory 202, user interface (UI) 204, communication circuitry 206, and sensors 208. In some examples, external device 30 may correspond to any of external devices 30A-30D described with respect to FIGS. 1, 2, and 4A-5. External device 30 may be a dedicated hardware device with dedicated software for the programming and/or interrogation of an IMD 10. Alternatively, external device 30 may be an off-the-shelf computing device, e.g., a smart phone running a mobile application that enables external device 30 to program and/or interrogate IMD 10. In some examples where external device 30 is a smart phone, external device 30 may include a mobile application to facilitate interaction with IMD 10. In some examples, external device 30 may be a wearable device, such as a smart watch or fitness tracker.

In some examples, a user of external device 30 may be clinician, physician, heath care giver, patient, family member of the patient or friend of the patient. In some examples, a user uses external device 30 to select or program any of the values for operational parameters of IMD 10. In some examples, a user uses external device 30 to receive data collected by IMD 10, such as when a person is walking 174, when the person is talking 176, a risk of falling 178, or other operational and performance data of IMD 10. In some examples, the user may also receive alerts provided by IMD 10 that indicate that an acute cardiac event, e.g., ventricular tachyarrhythmia, is predicted. In some examples, IMD 10 may transmit an alert and the user may also receive an alert that the patient may be more likely to fall or that the patient needs attention. The user may interact with external device 30 via UI 204, which may include a display to present a graphical user interface to a user, and a keypad or another mechanism (such as a touch sensitive screen) for receiving input from a user. External device 30 may communicate wirelessly with IMD 10 using communication circuitry 206, which may be configured for RF communication with communication circuitry 168 of IMD 10. Sensors 208 may include accelerometer circuitry 212 (shown as ACCLRM 212) and/or microphone 210 (shown as MIC 210). Accelerometer circuitry 212 may be configured to generate at least one signal indicative of when a person is walking. Microphone 210 may be configured to capture a voice of a person.

Processing circuitry 200 may include any combination of integrated circuitry, discrete logic circuitry, analog circuitry, such as one or more microprocessors, digital signal processors (DSPs), application specific integrated circuits (ASICs), or field-programmable gate arrays (FPGAs). In some examples, processing circuitry 200 may include multiple components, such as any combination of one or more microprocessors, one or more DSPs, one or more ASICs, or one or more FPGAs, as well as other discrete or integrated logic circuitry, and/or analog circuitry. Processing circuitry 200 may be communicatively coupled elements of external device 30 such as memory 202, accelerometry circuitry 212, and microphone 210.

Memory 202 may store program instructions, which may include one or more program modules, which are executable by processing circuitry 200. When executed by processing circuitry 200, such program instructions may cause processing circuitry 200 and external device 30 to provide the functionality ascribed to them herein. The program instructions may be embodied in software, firmware and/or RAMware. Memory 202 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital media.

In some examples, processing circuitry 200 of external device 30 may be configured to provide some or all of the functionality ascribed to processing circuitry 160 of IMD 10 herein. For example, processing circuitry 200 may receive at least one signal indicative of a person walking from IMD 10 or from accelerometer 212. Processing circuitry 200 may also receive a captured voice from IMD 10 or from microphone 210. Processing circuitry 200 may determine when the person is walking based on the at least one signal. Processing circuitry 200 determine when the person is talking based on the captured voice. Processing circuitry 200 may determine a risk of falling based on the determination of when the person is walking and the determination of when the person is talking.

Figure 9:
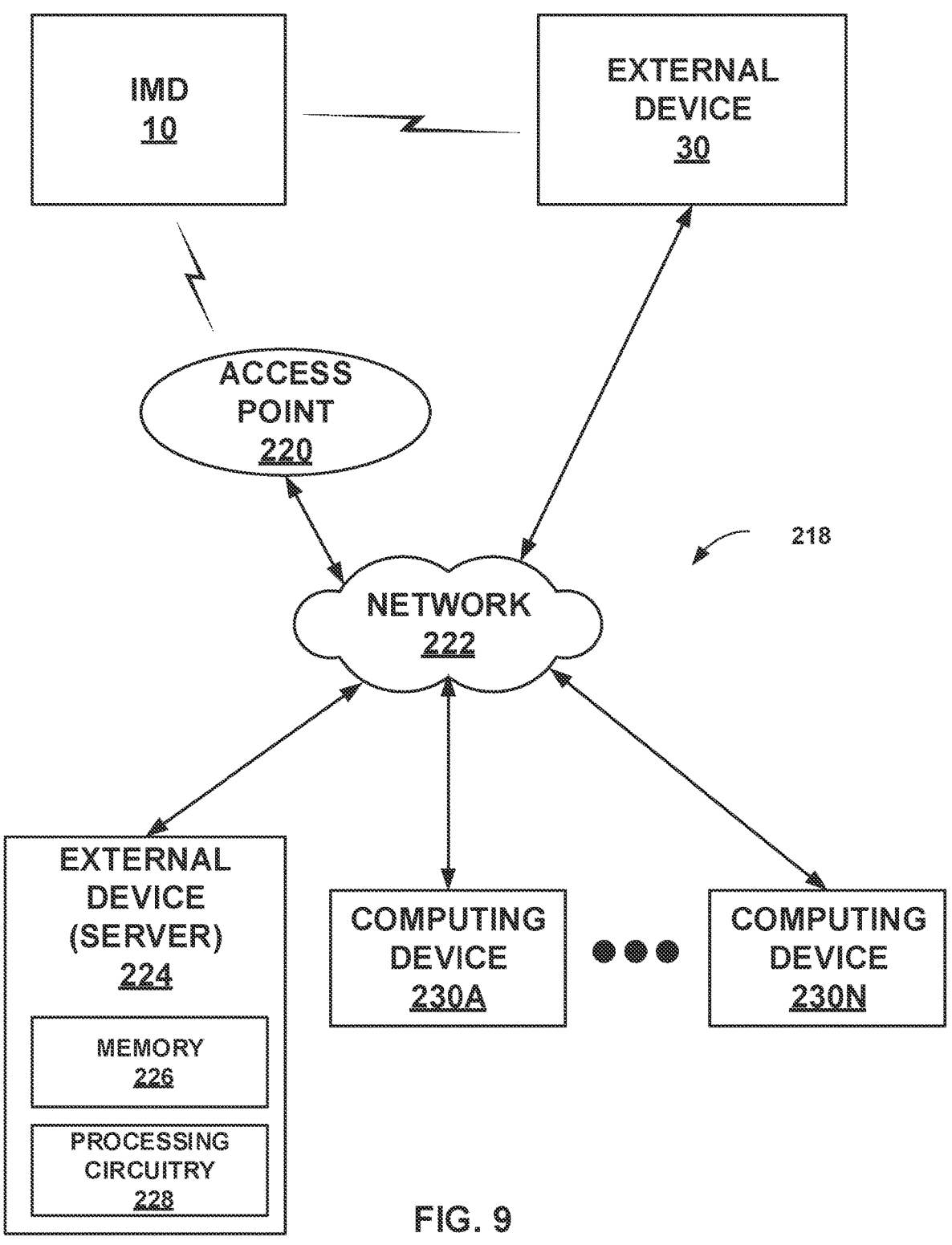
FIG. 9 is a functional block diagram illustrating an example system that includes remote computing devices, such as a server and one or more other computing devices, that are connected to an implantable medical device and/or external device via a network.

FIG. 9 is a functional block diagram illustrating an example system that includes external computing devices, such as a server 224 and one or more other computing devices 230A-230N, that are coupled to IMD 10 and external device 30 via a network 222. In this example, IMD 10 may use its communication circuitry 168 to, e.g., at different times and/or in different locations or settings, communicate with external device 30 via a first wireless connection, and to communication with an access point 220 via a second wireless connection. In the example of FIG. 9, access point 220, external device 30, server 224, and computing devices 230A-230N are interconnected, and able to communicate with each other, through network 222.

Access point 220 may comprise a device that connects to network 222 via any of a variety of connections, such as telephone dial-up, digital subscriber line (DSL), or cable modem connections. In other examples, access point 220 may be coupled to network 222 through different forms of connections, including wired or wireless connections. In some examples, access point 220 may be co-located with patient 14. Access point 220 may interrogate IMD 10, e.g., periodically or in response to a command from patient 14 or network 222, to retrieve physiological signals, when a person is walking 174, when a person is talking 176, a risk of falling 178, alerts of acute cardiac events, and/or other operational or patient data from IMD 10. Access point 220 may provide the retrieved data to server 224 via network 222.

In some cases, server 224 may be configured to provide a secure storage site for data that has been collected from IMD 10 and/or external device 30. In some cases, server 224 may assemble data in web pages or other documents for viewing by trained professionals, such as clinicians, via computing devices 230A-230N. The illustrated system of FIG. 9 may be implemented, in some aspects, with general network technology and functionality similar to that provided by the Medtronic CareLink® Network developed by Medtronic plc, of Dublin, Ireland.

In some examples, one or more of access point 220, server 224, or computing devices 230 may be configured to perform, e.g., may include processing circuitry configured to perform, some or all of the techniques described herein, e.g., with respect to processing circuitry 160 of IMD 10 and processing circuitry 200 of external device 30, relating to determining when a person is walking, when a person is talking, and a risk of falling. In the example of FIG. 9, server 224 includes a memory 226 to store signals or risk of falling 178 received from IMD 10 and/or external device 30, and processing circuitry 228, which may be configured to provide some or all of the functionality ascribed to processing circuitry 160 of IMD 10 and processing circuitry 200 of external device 30 herein. For example, processing circuitry 228 may determine risk of falling 178, and/or may receive risk of falling 178 from one or more IMDs 10 or external device 30. Processing circuitry 228 may determine when a person is walking 174, when the person is talking 176, and/or a risk of falling 178 in the manner described above with respect to processing circuitry 160 of IMD 10.

Figure 10:
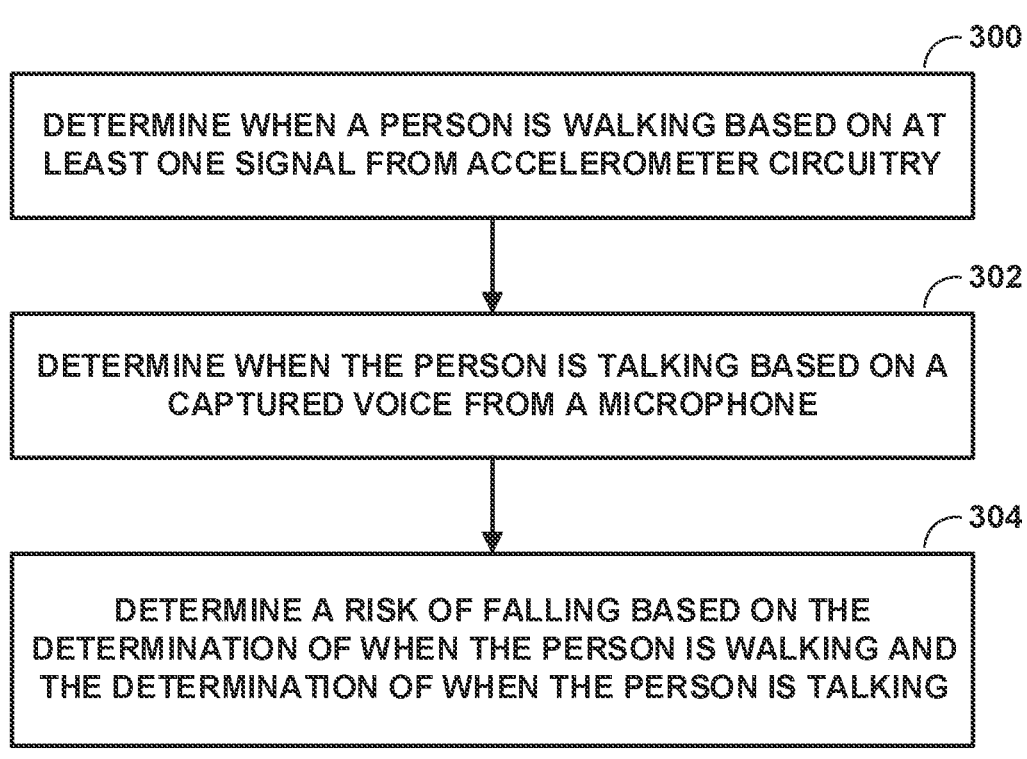
FIG. 10 is a flowchart illustrating an example determination of a risk of falling according to the techniques of this disclosure.

FIG. 10 is a flowchart illustrating an example of determining a risk of a person falling according to the techniques of this disclosure. This example may be implemented by any one of the IMDs discussed above in connection with FIGS. 1-9, because each one of the same is configured to include accelerometer circuitry and a microphone, as well as communication and processing circuitry (see FIG. 7 and corresponding description) to facilitate determining a risk of a person falling based on accelerometer circuitry-generated signal(s) and a captured voice. This example may also be implemented by an external medical device or any implantable or external device having at least one accelerometer and a microphone.

IMD 10 (FIG. 7) may determine when a person (e.g., patient 14 hear) is walking based on at least one signal from accelerometer circuitry 167 (300). IMD 10 may utilize an on-board accelerometer signal to determine that a person is walking. This signal may be one or more of a sagittal axis signal, a vertical axis signal and a transverse axis signal. IMD 10 may store a start time and an end time of the walking in when a person is walking 174.

IMD 10 may determine when the person is talking based on a captured voice from a microphone (302). For example, IMD 10 may compare the captured voice to a voice template 180 stored in memory 170 and when the captured voice matches voice template 180, store a start time and an end time of the talking in when a person is talking 176. In some examples, IMD 10 may continually monitor signals captured by microphone 165 and compare the signals to voice template 180. In some examples, IMD 10 may only monitor signals captured by microphone 165 when IMD 10 determines that a person is walking. In this manner, IMD 10 may save battery power when compared to continually monitoring signals captured by microphone 165.

IMD 10 may determine a risk of falling based on the determination of when the person is walking and the determination of when the person is talking (304). For example, IMD 10 may compare the times when the person is walking to the times when the person is talking and determine a risk that the person may fall based on the comparison. In some examples, IMD 10 may store, in memory 170, a start time and a stop time of the determined walking (e.g., when person is walking 174) and store, in memory 170, a start time and a stop time of the determined talking (e.g., when person is talking 176). In some examples, IMD 10 may determine the risk of falling by comparing the start time and the stop time of the determined walking to the start time and the stop time of the determined talking and determining an amount of overlap in the determined walking and the determined talking based on the comparison. In some examples, IMD 10 may determine the risk of falling based on the determined amount of overlap. In some examples, IMD 10 may store the risk of falling in memory 170 (e.g., risk of falling 178).

For example, if there is an overlap in the walking and talking times, IMD 10 may determine that the risk of falling is low. If there is not an overlap in the walking and talking times, IMD 10 may determine that the risk of falling is high. In some examples, rather than a low or high determination, IMD 10 may determine a risk of falling score based on a summation of the amount of overlap in the walking and talking times. For example, IMD 10 may monitor for overlapping walking and talking times. IMD 10 may sum such overlapping times for each day and create a walking and talking baseline over a predetermined period of time. For example, the baseline may be the median of overlapping walking and talking times from the previous 13 days. IMD 10 may compare subsequent daily overlapping walking and talking times to the baseline. Because each person's personality or number of acquaintances will impact their opportunity for walking and talking at the same time, using a personalized baseline would normalize the detection of a risk of falling across people. For example, IMD 10 may perform a Statistical Process Control analysis which may show a person's percentile rank of overlapping walking and talking times compared to past measurements. The higher the percentile above baseline (more overlap), the less risk the patient may have of falling. The lower the percentile, the greater risk the patient may have of falling. In some examples, a high risk of falling score may be based on sustained low overlapping walking and talking times over a predetermined period of time, such as several days.

In some examples, the risk of falling score may be on a scale of 1-5, 1-10, 1-100, or some other scale. For example, if there is complete overlap of the walking and talking times, the risk of falling may be at the low side of the scale, 1, for example. If there is no overlap of walking and talking times, the risk of falling may be at the high side of the risk of falling scale, 100, for example.

In some examples, IMD 10 may determine a risk of falling score based on the amount of overlap in the walking and talking times and the amount of walking time and/or the amount of talking time. For example, if there is an hour of walking, three hours of talking, and an overlap of walking and talking of 30 minutes, IMD 10 may determine the risk of falling to be near the low end of the risk of falling scale, 5, for example. For example, IMD 10 may allow for time for responsive talking by other individuals, as it may be unlikely that a person would speak for a long period of time without stopping their speech to listen for a response from another individual.

In some examples, external device 30 (FIG. 8) may communicate, via user interface 204, the risk of falling score to a user. In some examples, IMD 10 may transmit, via communication circuitry 168, an alert including the risk of falling score to a clinician device (e.g., external device 30). In some examples, IMD 10 may determine a new risk of falling score and determine a level of efficacy of an intervention of a clinician after the intervention based on the new risk of falling score, wherein the intervention is in response to the transmitted alert. In some examples, IMD 10 may determine the risk of falling on a periodic basis, such as daily, weekly, monthly, etc.

For example, if IMD 10 determines the risk of falling to be relatively high or higher than a predetermined threshold, IMD 10 may send an alert to external device 30, or a computing device 230, as examples. The alert may inform the recipient that patient 14 is likely to fall. This may be indicative of deteriorating health, illness or loss of lower body and/or core strength. By sending the alert, IMD 10 may enable someone to intervene to assist patient 14.

In some examples, a clinician may intervene to attempt to improve the condition of patient 14. The techniques of FIG. 10 may then be used to determine the efficacy of the intervention.

By monitoring times when a person (such as patient 14) is walking and times when a person is talking, a device (such as IMD 10 or external device 30) may determine a risk that the person may fall. This determined risk may be used by a clinician to intervene and avert a potential fall.

Example 1. A system comprising: accelerometer circuitry configured to generate at least one signal indicative of a person walking; a microphone configured to capture a voice of the person; a memory; and processing circuitry communicatively coupled to the accelerometer circuitry, the microphone, and the memory configured to: determine when the person is walking based on the at least one signal; determine when the person is talking based on the captured voice; and determine a risk of falling based on the determination of when the person is walking and the determination of when the person is talking.

Example 2. The system of Example 1, wherein as part of determining when the person is talking, the processing circuitry is configured to compare the captured voice to a voice template stored in the memory.

Example 3. The system of Example 1 or 2, wherein the processing circuitry is further configured to: store, in the memory, a start time and a stop time of the determined walking; and store, in the memory, a start time and a stop time of the determined talking.

Example 4. The system of Example 3, wherein as part of determining the risk of falling, the processing circuitry is configured to: compare the start time and the stop time of the determined walking to the start time and the stop time of the determined talking; and determine an amount of overlap in the determined walking and the determined talking based on the comparison.

Example 5. The system of Example 4, wherein as part of determining the risk of falling, the processing circuitry is configured to determine a risk of falling score based on the determined amount of overlap.

Example 6. The system of Example 5, further comprising a user interface configured to communicate the risk of falling score to a user.

Example 7. The system of Example 5 or 6, further comprising communication circuitry configured to transmit an alert comprising the risk of falling score to a clinician device.

Example 8. The system of Example 7, wherein the processing circuitry is further configured to: determine a new risk of falling score; and determine a level of efficacy of an intervention of a clinician after the intervention based on the new risk of falling score, wherein the intervention is in response to the transmitted alert.

Example 9. The system of any of Examples 1-8, wherein as part of determining when the person is talking, the processing circuitry is configured to continuously monitor a signal from the microphone.

Example 10. The system of any of Examples 1-9, wherein the processing circuitry is configured to determine the risk of falling on a periodic basis.

Example 11. A method comprising: determining, by processing circuitry, when a person is walking based on at least one signal from accelerometer circuitry; determining, by processing circuitry, when the person is talking based on a captured voice from a microphone; and determining a risk of falling based on the determination of when the person is walking and the determination of when the person is talking.

Example 12. The method of Example 11, wherein determining when the person is talking comprises comparing the captured voice to a voice template stored in memory.

Example 13. The method of Example 11 or 12, further comprising: storing, in memory, a start time and a stop time of the determined walking; and storing, in memory, a start time and a stop time of the determined talking.

Example 14. The method of Example 13, wherein determining the risk of falling comprises: comparing the start time and the stop time of the determined walking to the start time and the stop time of the determined talking; and determining an amount of overlap in the determined walking and the determined talking based on the comparison.

Example 15. The method of Example 14, wherein determining the risk of falling comprises determining a risk of falling score based on the determined amount of overlap.

Example 16. The method of Example 15, further comprising: communicating, via a user interface, the risk of falling score to a user.

Example 17. The method of Example 15 or 16, further comprising: transmitting, via communication circuitry, an alert comprising the risk of falling score to a clinician device.

Example 18. The method of Example 17, further comprising: determining a new risk of falling score; and determining a level of efficacy of an intervention of a clinician after the intervention based on the new risk of falling score, wherein the intervention is in response to the transmitted alert.

Example 19. The method of any of Examples 11-18, wherein the determining the risk of falling is performed on a periodic basis.

Example 20. A non-transitory computer-readable storage medium comprising instructions, that when executed by processing circuitry of a device, cause the device to: determine when a person is walking based on at least one signal for accelerometer circuitry; determine when the person is talking based on a captured voice from a microphone; and determine a risk of falling based on the determination of when the person is walking and the determination of when the person is talking.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including an IMD, an external programmer, a combination of an IMD and external programmer, an integrated circuit (IC) or a set of ICs, and/or discrete electrical circuitry, residing in an IMD and/or external programmer.

Various aspects of the disclosure have been described. These and other aspects are within the scope of the following claims.

What is claimed is:

1. A system comprising:

accelerometer circuitry configured to generate at least one signal indicative of a person walking;

a microphone configured to capture a voice of the person;

a memory; and processing circuitry communicatively coupled to the accelerometer circuitry, the microphone, and the memory configured to:

determine when the person is walking based on the at least one signal;

store, in the memory, a start time and a stop time of the determined walking;

determine when the person is talking based on the captured voice;

store, in the memory, a start time and a stop time of the determined talking;

compare the start time and the stop time of the determined walking to the start time and the stop time of the determined talking;

determine an amount of overlap in the determined walking and the determined talking based on the comparison;

determine a risk of falling based on the amount of overlap in the determined walking and the determined talking; and output an indication of the risk of falling.

2. The system of claim 1, wherein as part of determining when the person is talking, the processing circuitry is configured to compare the captured voice to a voice template stored in the memory.

3. The system of claim 1, wherein as part of determining the risk of falling, the processing circuitry is configured to determine a risk of falling score based on the determined amount of overlap.

4. The system of claim 3, further comprising a user interface configured to output the indication of the risk of falling, wherein to output the indication of the risk of falling, the user interface is configured to communicate the risk of falling score to a user.

5. The system of claim 3, further comprising communication circuitry configured to output the indication of the risk of falling, wherein to output the indication of the risk of falling, the communication circuitry is configured to transmit an alert comprising the risk of falling score to a clinician device.

6. The system of claim 5, wherein the processing circuitry is further configured to:

determine a new risk of falling score; and determine a level of efficacy of an intervention of a clinician after the intervention based on the new risk of falling score, wherein the intervention is in response to the transmitted alert.

7. The system of claim 1, wherein as part of determining when the person is talking, the processing circuitry is configured to continuously monitor a signal from the microphone.

8. The system of claim 1, wherein the processing circuitry is configured to determine the risk of falling on a periodic basis.

9. A method comprising:

determining, by processing circuitry, when a person is walking based on at least one signal from accelerometer circuitry;

storing, in memory, a start time and a stop time of the determined walking;

determining, by processing circuitry, when the person is talking based on a captured voice from a microphone;

storing, in memory, a start time and a stop time of the determined talking;

comparing the start time and the stop time of the determined walking to the start time and the stop time of the determined talking;

determining an amount of overlap in the determined walking and the determined talking based on the comparison;

determining a risk of falling based on the amount of overlap in the determined walking and the determined talking; and outputting an indication of the risk of falling.

10. The method of claim 9, wherein determining when the person is talking comprises comparing the captured voice to a voice template stored in memory.

11. The method of claim 9, wherein determining the risk of falling comprises determining a risk of falling score based on the determined amount of overlap.

12. The method of claim 11, wherein outputting the indication of the risk of falling comprises:

communicating, via a user interface, the risk of falling score to a user.

13. The method of claim 11, wherein outputting the indication of the risk of falling comprises:

transmitting, via communication circuitry, an alert comprising the risk of falling score to a clinician device.

14. The method of claim 13, further comprising:

determining a new risk of falling score; and determining a level of efficacy of an intervention of a clinician after the intervention based on the new risk of falling score, wherein the intervention is in response to the transmitted alert.

15. The method of claim 9, wherein the determining the risk of falling is performed on a periodic basis.

16. A non-transitory computer-readable storage medium comprising instructions, that when executed by processing circuitry of a device, cause the device to:

determine when a person is walking based on at least one signal for accelerometer circuitry;

store, in a memory, a start time and a stop time of the determined walking;

determine when the person is talking based on a captured voice from a microphone;

store, in the memory, a start time and a stop time of the determined talking;

compare the start time and the stop time of the determined walking to the start time and the stop time of the determined talking;

determine an amount of overlap in the determined walking and the determined talking based on the comparison;

determine a risk of falling based on the amount of overlap in the determined walking and the determined talking; and output an indication of the risk of falling.

* * * * *